US012697451B2

(12) United States Patent
Plott et al.

(10) Patent No.: US 12,697,451 B2
(45) Date of Patent: Aug. 4, 2026

(54) NASOPHARYNGEAL AIRWAY DEVICES

(71) Applicant: REGENTS OF THE UNIVERSITY OF MICHIGAN, Ann Arbor, MI (US)

(72) Inventors: Jeffrey Stephen Plott, Algonac, MI (US); Dian-Ru Li, Ann Arbor, MI (US); David Adam Zopf, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 921 days.

(21) Appl. No.: 17/773,415

(22) PCT Filed: Nov. 4, 2020

(86) PCT No.: PCT/US2020/058860
§ 371 (c)(1),
(2) Date: Apr. 29, 2022

(87) PCT Pub. No.: WO2021/091998
PCT Pub. Date: May 14, 2021

(65) Prior Publication Data
US 2022/0378598 A1     Dec. 1, 2022

Related U.S. Application Data

(60) Provisional application No. 62/930,344, filed on Nov. 4, 2019.

(51) Int. Cl.
A61M 16/04          (2006.01)
A61F 5/08            (2006.01)
A61M 29/00          (2006.01)

(52) U.S. Cl.
CPC ........... A61M 16/0461 (2013.01); A61F 5/08 (2013.01); A61M 29/00 (2013.01)

(58) Field of Classification Search
CPC .. A61M 16/00; A61M 16/04; A61M 16/0402; A61M 16/0431; A61M 16/0461;
(Continued)

(56) References Cited

U.S. PATENT DOCUMENTS 3,260,258 A * 7/1966 Berman ............ A61M 16/0666
                                                            604/93.01
3,867,946 A 2/1975 Huddy
(Continued)

FOREIGN PATENT DOCUMENTS

CN     201366163 Y     12/2009
CN     111790034 A     10/2020
(Continued)

OTHER PUBLICATIONS

Extended European Search Report for Application No. 20884526.3, dated Nov. 27, 2023.
(Continued)

*Primary Examiner* — Colin W Stuart
(74) *Attorney, Agent, or Firm* — MARSHALL, GERSTEIN & BORUN LLP

(57)          ABSTRACT

A nasopharyngeal airway device includes an elongate body having a distal end and a proximal end. The elongate body has an outer surface defining one or more open channels extending along the elongate body. The nasopharyngeal airway device includes a securement component securely coupled to the elongate body. The securement component is configured to secure the nasopharyngeal airway device within a nostril of an individual.

12 Claims, 28 Drawing Sheets

(58) Field of Classification Search

CPC .......... A61M 16/0465; A61M 16/0475; A61M 16/0477; A61M 16/0486; A61M 16/0666

See application file for complete search history.

(56) References Cited

U.S. PATENT DOCUMENTS

| | | | | |
|---|---|---|---|---|
| 4,175,564 | A | * | 11/1979 | Kwak ................. A61J 15/0026 604/540 |
| 4,398,910 | A | | 8/1983 | Blake et al. |
| 4,465,481 | A | | 8/1984 | Blake |
| 4,821,715 | A | * | 4/1989 | Downing .......... A61M 16/0461 128/207.18 |
| 5,664,567 | A | * | 9/1997 | Linder .............. A61M 16/0477 128/911 |
| 6,183,493 | B1 | | 2/2001 | Zammit |
| 8,241,316 | B2 | | 8/2012 | Oberle |
| 10,391,272 | B1 | | 8/2019 | Vilasi et al. |
| 11,400,244 | B2 | * | 8/2022 | Beck ......................... A61F 5/08 |
| 2004/0006331 | A1 | * | 1/2004 | Shchervinsky ....... A61M 27/00 604/541 |
| 2004/0176745 | A1 | | 9/2004 | Ferguson |
| 2006/0048775 | A1 | | 3/2006 | Dunlap |
| 2006/0085027 | A1 | | 4/2006 | Santin et al. |
| 2006/0283464 | A1 | * | 12/2006 | Dunlap ............. A61M 16/0461 128/206.28 |
| 2008/0053458 | A1 | | 3/2008 | De Silva et al. |
| 2008/0276938 | A1 | | 11/2008 | Jeppesen et al. |
| 2009/0005762 | A1 | | 1/2009 | Nishtala et al. |
| 2009/0165793 | A1 | | 7/2009 | Peck |
| 2009/0266365 | A1 | * | 10/2009 | Oberle ....................... A61F 5/56 128/207.18 |
| 2012/0080037 | A1 | | 4/2012 | Guyuron et al. |
| 2012/0318279 | A1 | | 12/2012 | Yamada et al. |
| 2013/0019872 | A1 | | 1/2013 | Guyuron et al. |
| 2013/0269692 | A1 | | 10/2013 | Barbut et al. |
| 2015/0231361 | A1 | | 8/2015 | O'Keefe et al. |
| 2015/0250966 | A1 | * | 9/2015 | Shabat .............. A61M 16/0465 128/200.26 |
| 2017/0281888 | A1 | * | 10/2017 | McMurray ........ A61M 16/0475 |
| 2021/0220590 | A1 | | 7/2021 | Zopf et al. |

FOREIGN PATENT DOCUMENTS

| | | | |
|---|---|---|---|
| GB | 2391812 | A | 2/2004 |
| KR | 2017-0010149 | A | 1/2017 |
| WO | WO-2009/096875 | A1 | 8/2009 |
| WO | WO-2011/013122 | A2 | 2/2011 |
| WO | WO-2016/128881 | A1 | 8/2016 |
| WO | WO-2019/070966 | A1 | 4/2019 |
| WO | WO-2019/222451 | A1 | 11/2019 |
| WO | WO-2021/091988 | A1 | 5/2021 |

OTHER PUBLICATIONS

International Search Report and Written Opinion for Application No. PCT/US2020/058860, mailed Mar. 16, 2021.

Cardinal Health, Jackson-Pratt Hemaduct Wound Drains brochure, Nov. 2, 2019.

International Search Report and Written Opinion, corresponding International Application No. PCT/US23/20188, mailing date Sep. 25, 2023, 19 pages.

* cited by examiner

700

708

704

707

702

117

704

711

710

106

712

NASOPHARYNGEAL AIRWAY DEVICES

CROSS-REFERENCE TO RELATED APPLICATION

This present application is the US national phase of International Patent Application No. PCT/US20/058860, filed Nov. 4, 2020, which claims priority and the benefit of the filing date of U.S. Provisional Patent Application No. 62/930,344, filed Nov. 4, 2019, which is hereby incorporated by reference in its entirety.

FIELD OF THE DISCLOSURE

The application relates generally to nasopharyngeal airway devices and, in particular, to nasopharyngeal airway devices having one or more tubeless airway portions.

BACKGROUND

Obstructive sleep apnea is a sleeping disorder during which breathing stops and starts due to occlusion of the airway. Some known sleep apnea treatments include providing an individual with a continuous positive airway pressure mask that encourages the airway to stay open through the delivery of pressurized air. These masks are bulky, noisy, and uncomfortable, and compliance is low.

Nasopharyngeal airway devices are used in some medical applications to encourage the airway of an individual to stay open. The conventional nasopharyngeal airway device may be inserted into the nose of the individual and provides a tube through which air can flow. Insertion of such a device may be uncomfortable, and mucus may have a tendency to occlude the tube of the device.

SUMMARY

This disclosure relates to open-channeled nasopharyngeal airway devices having a nontubular portion. The airway devices may be adapted to prevent mucus build-up. Thus, as a result, the airway devices disclosed may be tolerated in an indwelling condition for a longer duration than a tubular airway device. The open channels of the disclosed airway devices may disperse the air flow in a manner that deters the individual using the airway devices from obtaining a sore throat. The open channels of the airway devices may also be easier to clean than a tubular airway device. The open channels of the airway devices may be adapted to resist occlusion if the airway device is kinked or compressed. For example, compression of one of the channels may open an adjacent one of the channels. Moreover, the one or more channels may provide a continuous surface(s) that can slide past the nasal airway rather than many interrupted sections which could potentially catch themselves on nasal airway tissue.

In accordance with a first example, a nasopharyngeal airway device includes an elongate body having a distal end and a proximal end. The elongate body has an outer surface defining one or more open channels extending along the elongate body. The nasopharyngeal airway device includes a securement component securely coupled to the elongate body. The securement component is configured to secure the nasopharyngeal airway device within a nostril of an individual.

In accordance with a second example, a nasopharyngeal airway device includes an elongate body having a distal end and a proximal end. The elongate body includes a hub and a plurality of ribs. The ribs outwardly extend from the hub. The ribs define one or more channels extending along the elongate body. The nasopharyngeal airway device includes a projection securely coupled to the elongate body. The projection is adapted to secure the nasopharyngeal airway device within a nostril of an individual.

In accordance with a third example, a nasopharyngeal airway device includes a fluted body having a distal end and a proximal end. The nasopharyngeal airway device includes a projection attached to the fluted body. The projection is adapted to secure the nasopharyngeal airway device within a nostril of an individual.

In accordance with a fourth example, a nasopharyngeal airway device includes a pair of fluted bodies. Each fluted body having a distal end and a proximal end. The nasopharyngeal airway device includes a bridge coupling the fluted bodies.

In accordance with a fifth example, a nasopharyngeal airway device includes an elongate body having a distal end, a proximal end, a hub, and a plurality of radial walls. The plurality of radial walls are coupled to the hub and extend outwardly from the hub. Flow paths are defined between the radial walls. Each flow path has a lateral opening defined between the corresponding radial walls and extending longitudinally between the distal end and the proximal end. The distal end of the elongate body includes a tapered portion or a rounded portion.

In accordance with a sixth example, a method includes inserting a distal end of an open-channel body within a nasal airway of an individual. The open-channel body having the distal end, a proximal end, and a curvature. The method includes securing the open-channel body relative to the nasal airway.

In further accordance with the foregoing first, second, third, fourth, fifth, and/or sixth examples, an apparatus and/or method may further include any one or more of the following:

In accordance with one example, the one or more open channels include one or more tubeless airway portions.

In accordance with another example, the securement component includes a projection.

In accordance with another example, the projection is a fin extending toward the proximal end of the elongate body and adapted to be inserted into the nostril and to provide a biasing force to secure the nasopharyngeal airway device within the nostril.

In accordance with another example, the projection includes an arced arm having a distal foot and extending toward the distal end of the elongate body. A proximal end of the arm being securely coupled to the elongate body.

In accordance with another example, an arm-outer surface and a distal-end outer surface have a substantially similar radius.

In accordance with another example, the projection and the elongate body form a clip.

In accordance with another example, the one or more open channels extend along the elongate body from the distal end to the proximal end.

In accordance with another example, the one or more open channels extend longitudinally along at least a portion of the elongate body.

In accordance with another example, the one or more open channels extend longitudinally along at least half of the elongate body.

In accordance with another example, the one or more open channels extend longitudinally less than half of the elongate body.

In accordance with another example, the one or more open channels extend along the elongate body from the proximal end to a location beyond a midpoint of the elongate body.

In accordance with another example, the one or more open channels extend along the elongate body from the distal end.

In accordance with another example, at least a portion of the one or more channels has a contiguous lateral opening between the distal end and the proximal end.

In accordance with another example, the elongate body further includes a tubular portion.

In accordance with another example, the tubular portion includes the distal end of the elongate body.

In accordance with another example, the hub and the ribs are not disposed within at least a portion of the tubular portion.

In accordance with another example, the fluted body has a dimensional envelope and the projection is disposed outside of the dimensional envelope of the fluted body.

In accordance with another example, the projection extends away from a tangential plane that intersects an exterior surface of the fluted body.

In accordance with another example, the fluted body includes a hub and a plurality of radial walls. The plurality of radial walls being coupled to the hub and extend outwardly from the hub. Flow paths are defined between the radial walls.

In accordance with another example, each flow path has a lateral opening defined between the radial walls and extending longitudinally between the distal end and the proximal end.

In accordance with another example, each radial wall includes a distal flange.

In accordance with another example, the lateral openings are defined between adjacent distal flanges.

In accordance with another example, the distal flange includes an arced outer face.

In accordance with another example, the flow paths extend throughout a majority of the nasopharyngeal airway device.

In accordance with another example, the distal end of the elongate body includes a tapered portion or a rounded portion.

In accordance with another example, the distal end includes surface tension reducing protrusions.

In accordance with another example, further including a securement component securely coupled adjacent the proximal end of at least one of the fluted bodies. The securement component is adapted to secure the nasopharyngeal airway device relative to a nostril of an individual.

In accordance with another example, the distal end of at least one of the fluted bodies includes a tapered portion or a rounded portion.

In accordance with another example, the fluted bodies have different lengths.

In accordance with another example, the radial walls extend longitudinally from the distal end to the proximal end.

In accordance with another example, the radial walls extend longitudinally along at least half of the elongate body.

In accordance with another example, the radial walls extend along at least a portion of the elongate body.

In accordance with another example, the radial walls extend along the elongate body from the proximal end to a location beyond a midpoint of the elongate body.

In accordance with another example, each radial wall includes a distal flange. The lateral openings being defined between adjacent distal flanges. In accordance with another example, the one or more channels comprise at least one of a straight-channel portion and or a helical pattern portion.

In accordance with another example, the one or more channels comprises a single channel.

In accordance with another example, the elongate body includes edges having opposing inward facing stops that define a lateral opening.

In accordance with another example, the stops have at least one of flat surfaces or corresponding contours that are positioned to abut one another.

In accordance with another example, the elongate body has a smooth inner surface that defines the channel.

In accordance with another example, the elongate body has an inner surface that defines the channel having a spiral protrusion.

In accordance with another example, the elongate body has a lateral opening to the channel that extends longitudinally along at least half of the elongate body.

In accordance with another example, the elongate body includes edges that form the lateral opening and have cutouts and inward facing stops that are positioned to abut one another.

In accordance with another example, the cutouts have a trapezoidal shape.

In accordance with another example, the distal end has a chamfer.

In accordance with another example, the distal end has a partially-closed rounded end.

In accordance with another example, an inner surface of the elongate body defining the channel forms a stop adapted to be engaged by a suction device or an endoscope.

In accordance with another example, the distal end has a fully-closed rounded end.

In accordance with another example, an inner surface of the elongate body defining the channel forms a stop adapted to be engaged by a suction device or an endoscope.

In accordance with another example, further including packaging in which the nasopharyngeal airway device is disposed.

In accordance with another example, further including lubricant within the packaging or on the elongate body.

In accordance with another example, the lubricant includes a local anesthetic.

In accordance with another example, further including a second elongate body coupled to the elongate body via a bridge.

US 12,697,451 B2

5

Figure 4A:
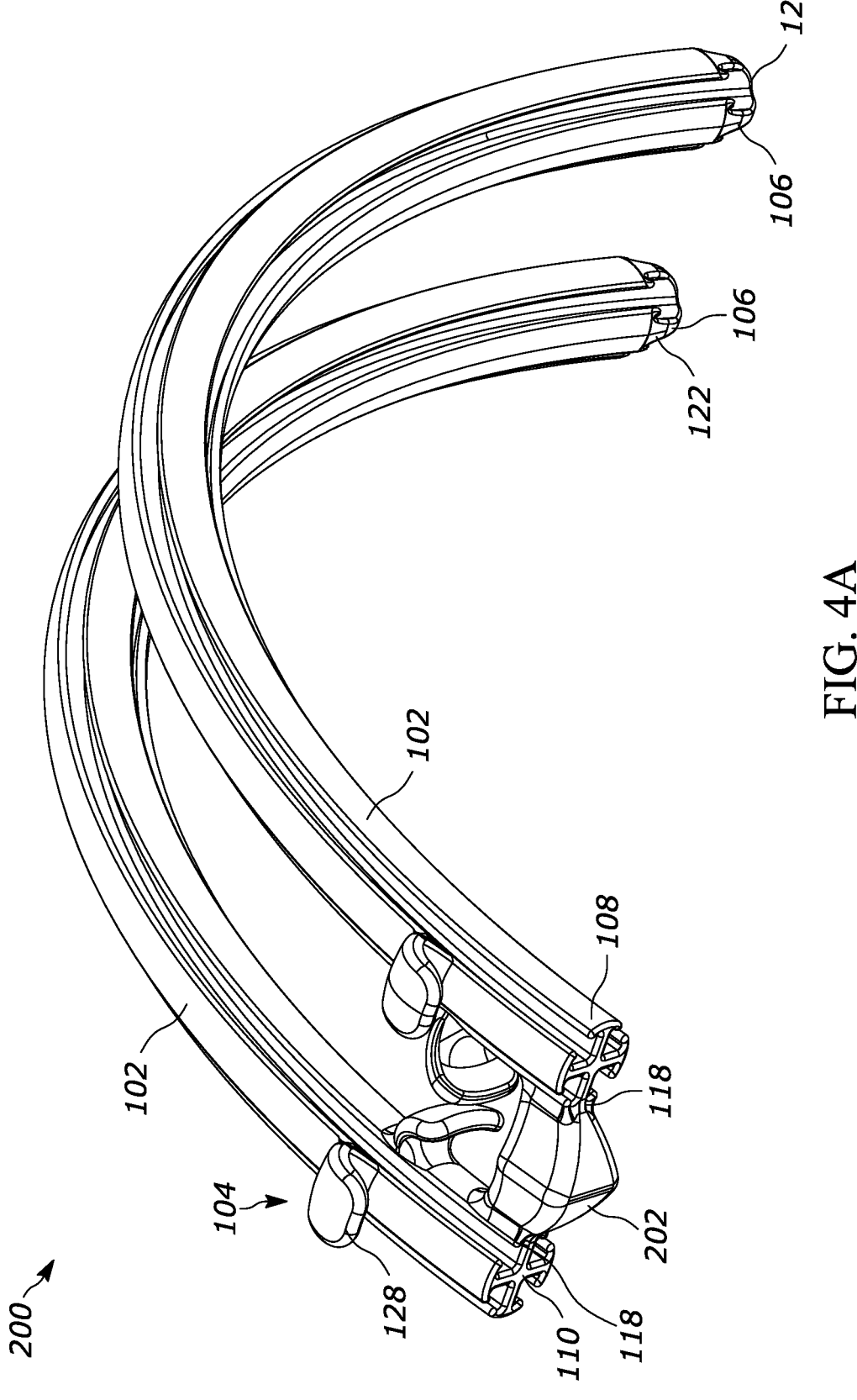

FIG. 4A is an isometric view of another nasopharyngeal airway device in accordance with a second example of the present disclosure.

Figure 4B:
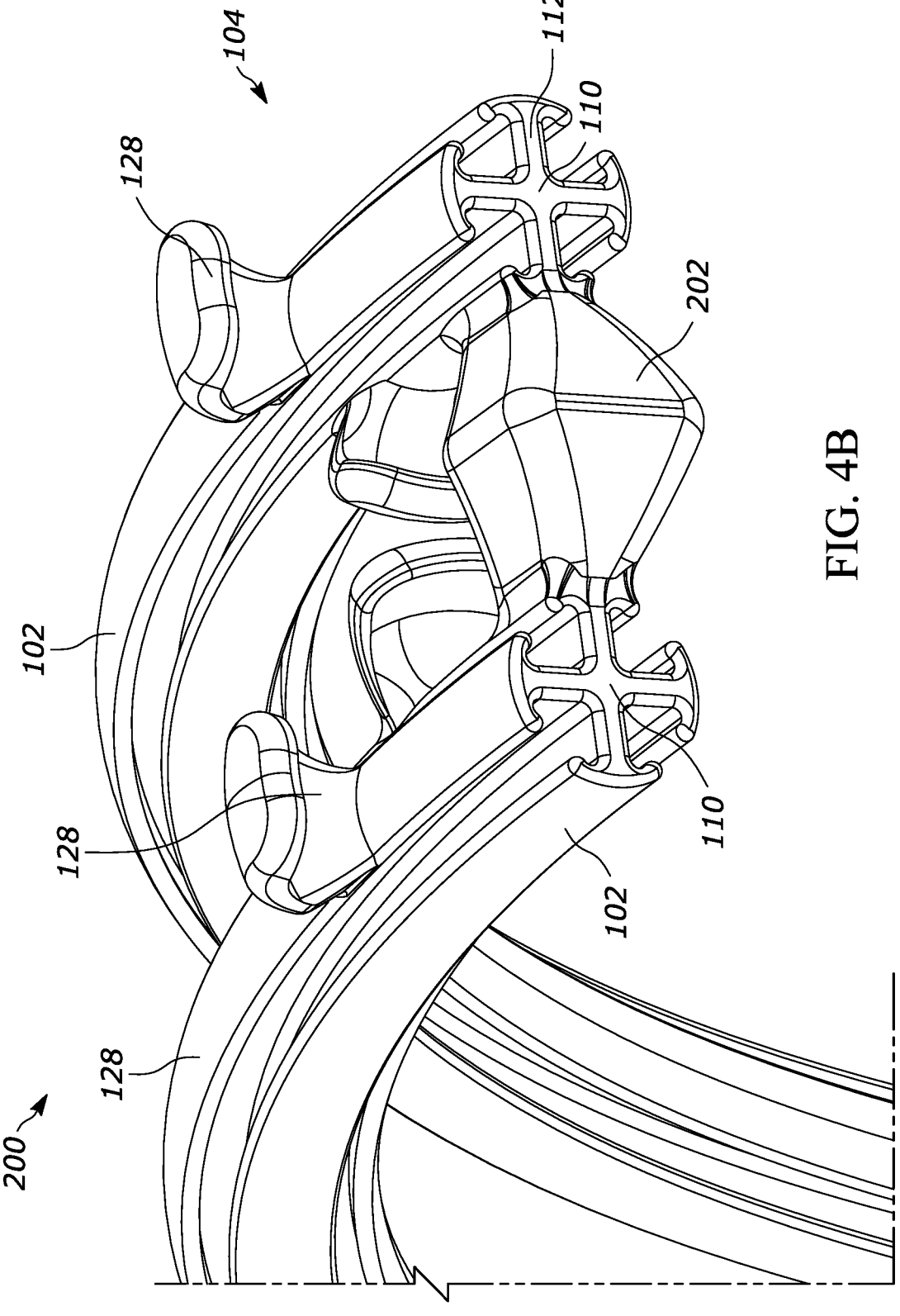

FIG. 4B is an enlarged isometric view of a proximal end of the nasopharyngeal airway device of FIG. 4A.

Figure 5:
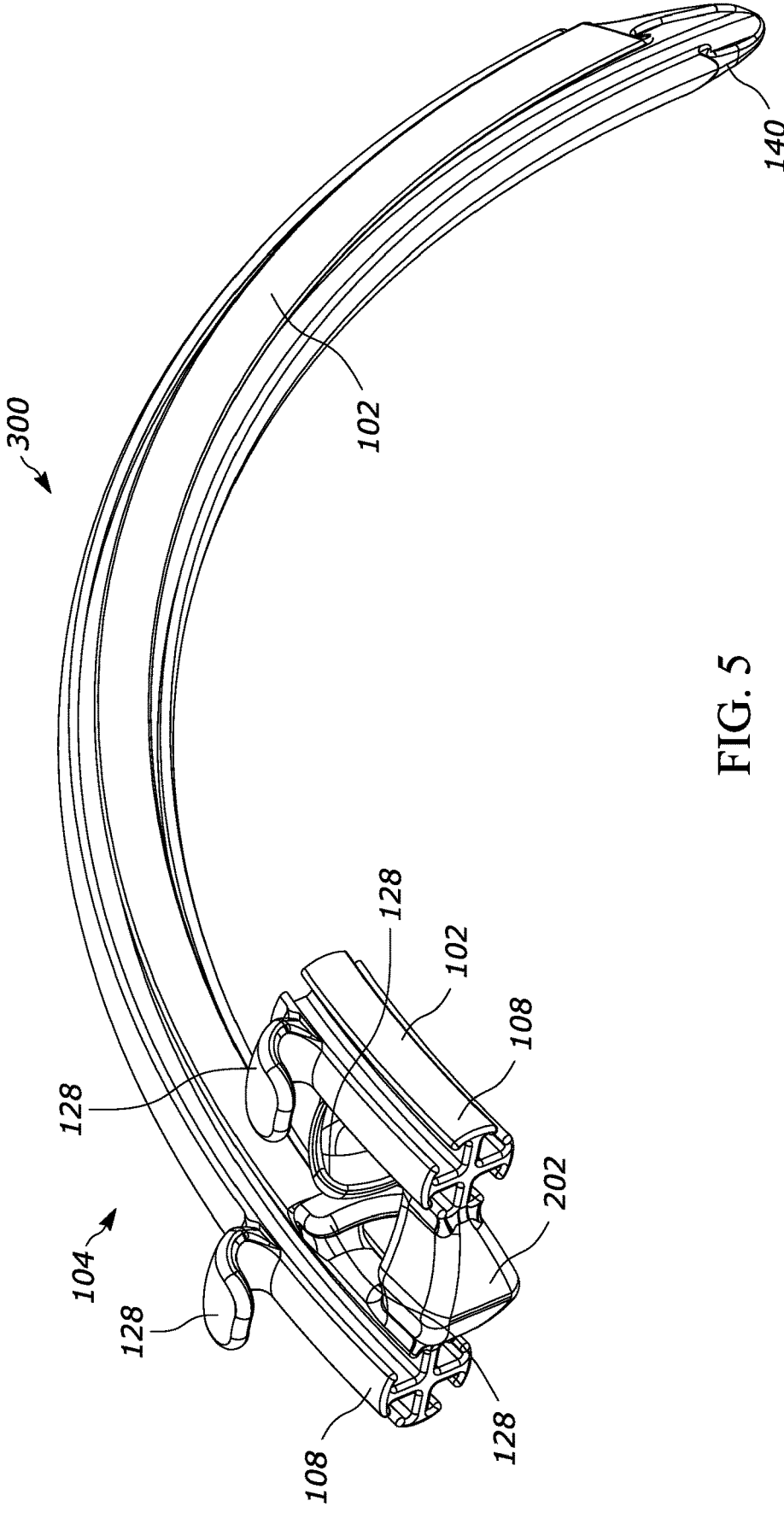

FIG. 5 is an isometric view of another nasopharyngeal airway device in accordance with a third example of the present disclosure.

Figure 6A:
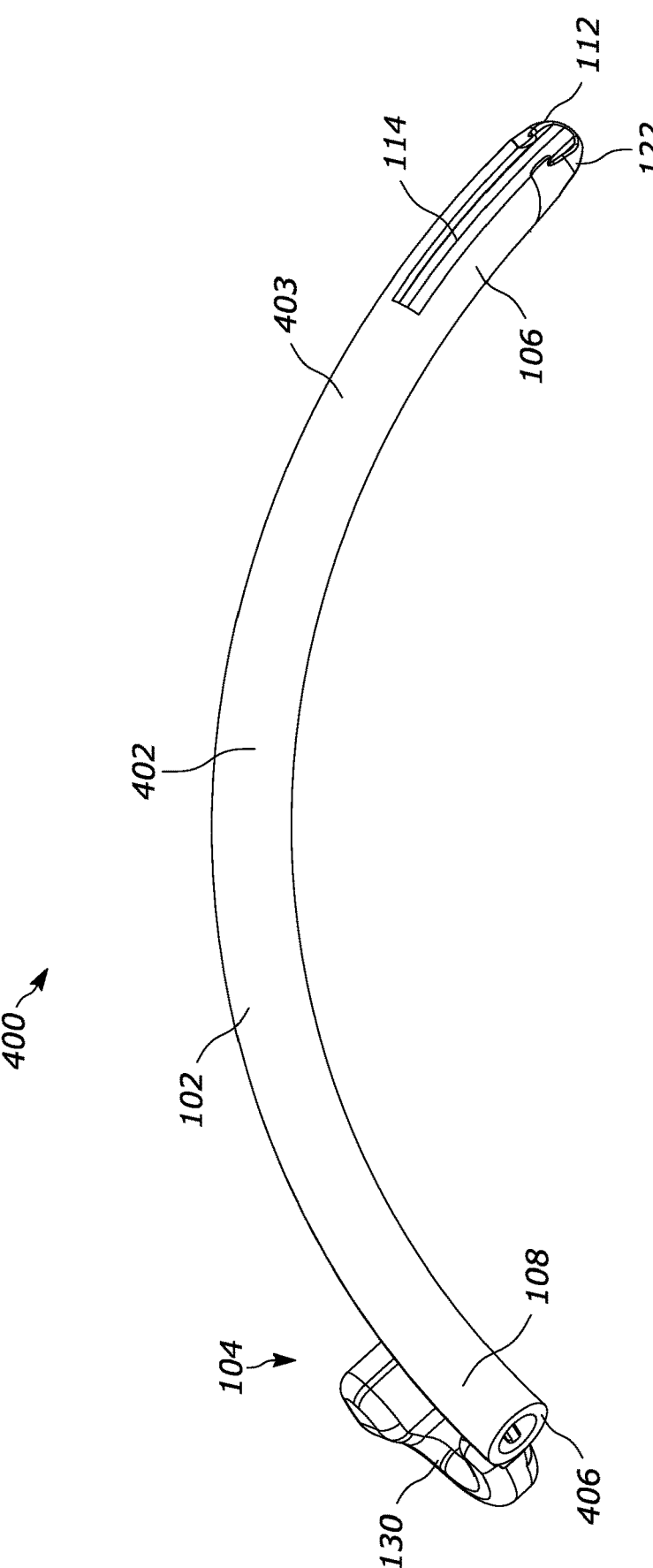

FIG. 6A is an isometric view of another nasopharyngeal airway device in accordance with a fourth example of the present disclosure.

Figure 6B:
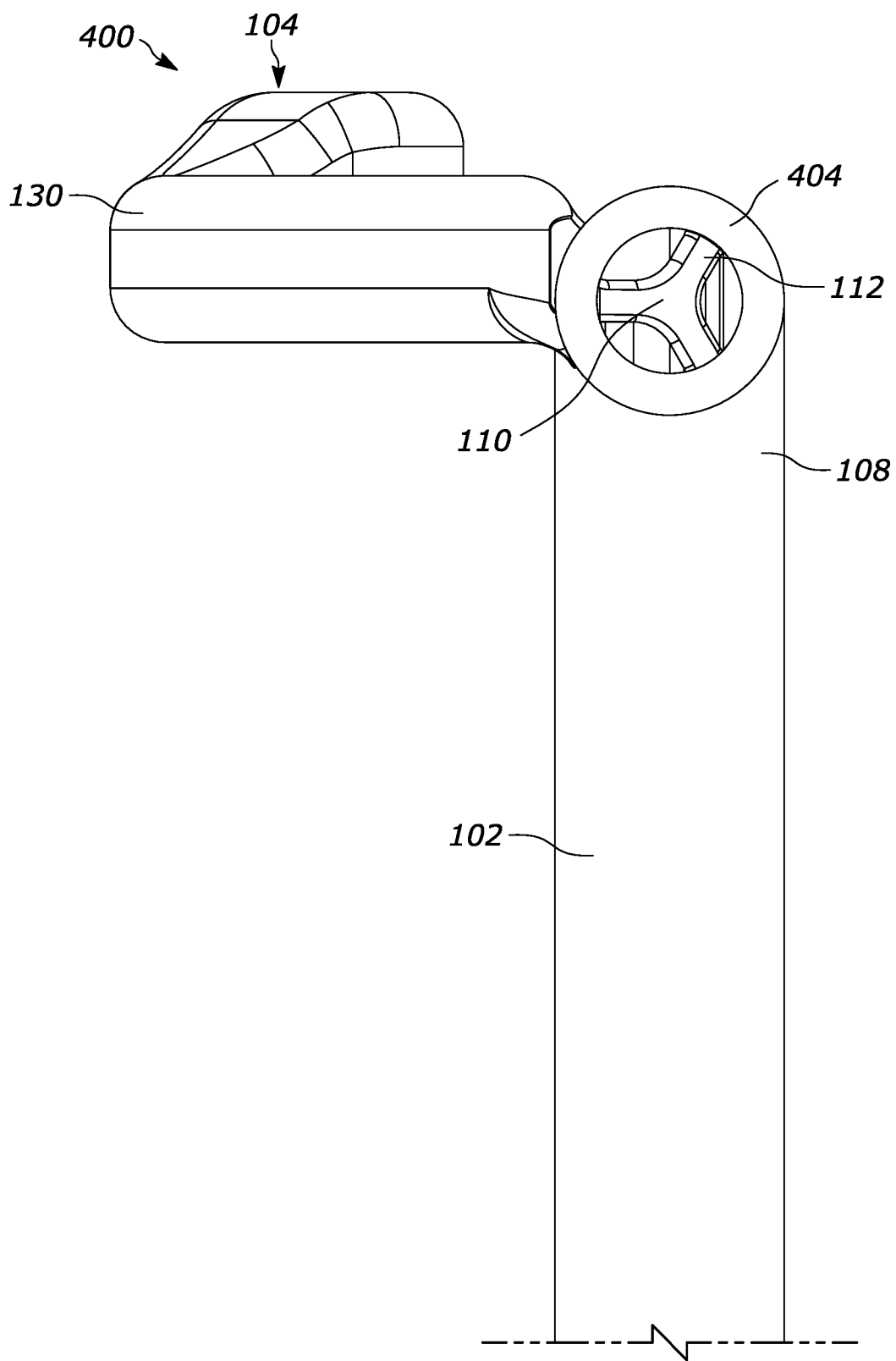

FIG. 6B is an enlarged isometric view of the proximal end of the nasopharyngeal airway device of FIG. 6A.

Figure 6C:
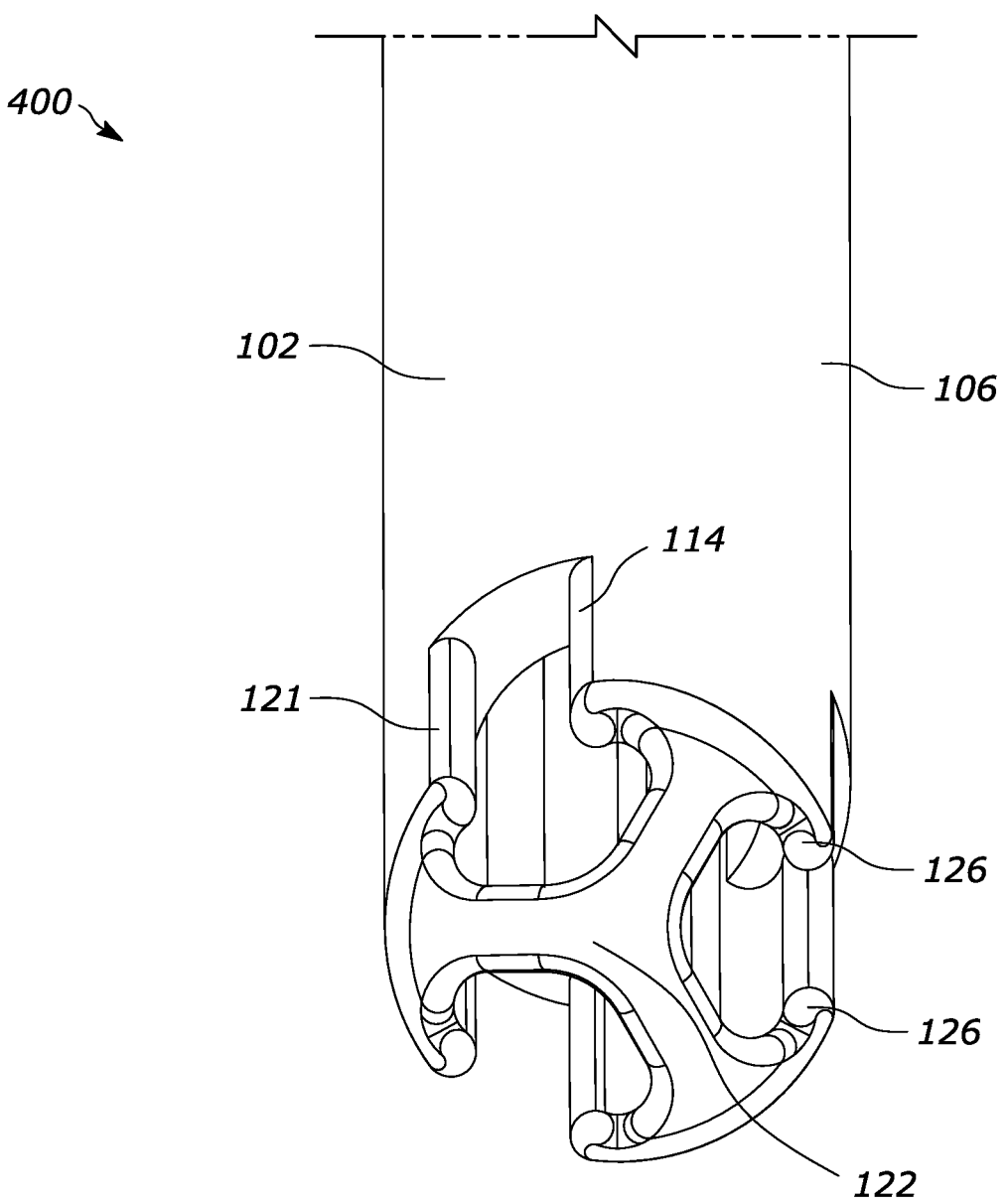

FIG. 6C is an enlarged isometric view of the distal end of the nasopharyngeal airway device of FIG. 6A.

Figure 7A:
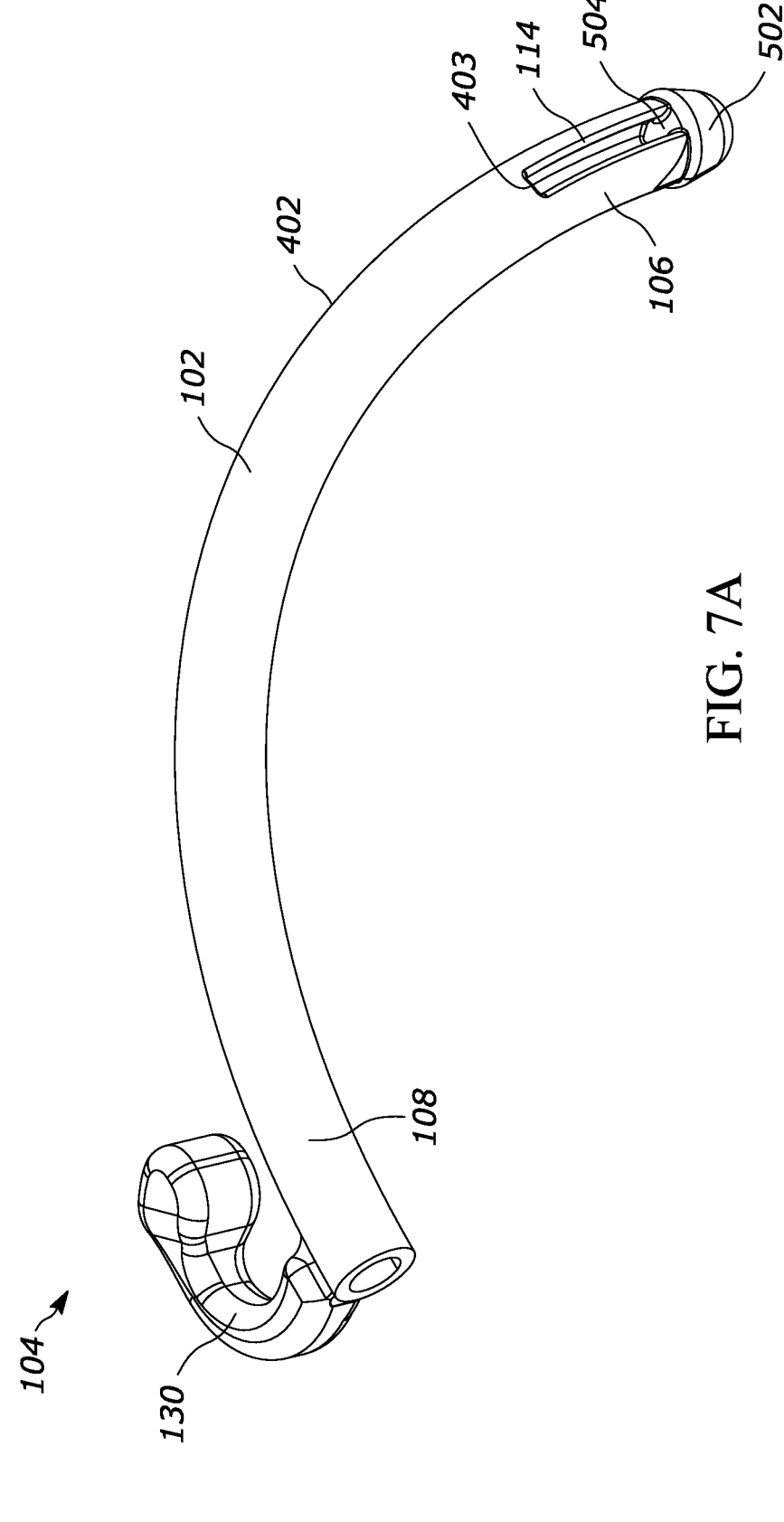

FIG. 7A is an isometric view of another nasopharyngeal airway device in accordance with a fifth example of the present disclosure.

Figure 7B:
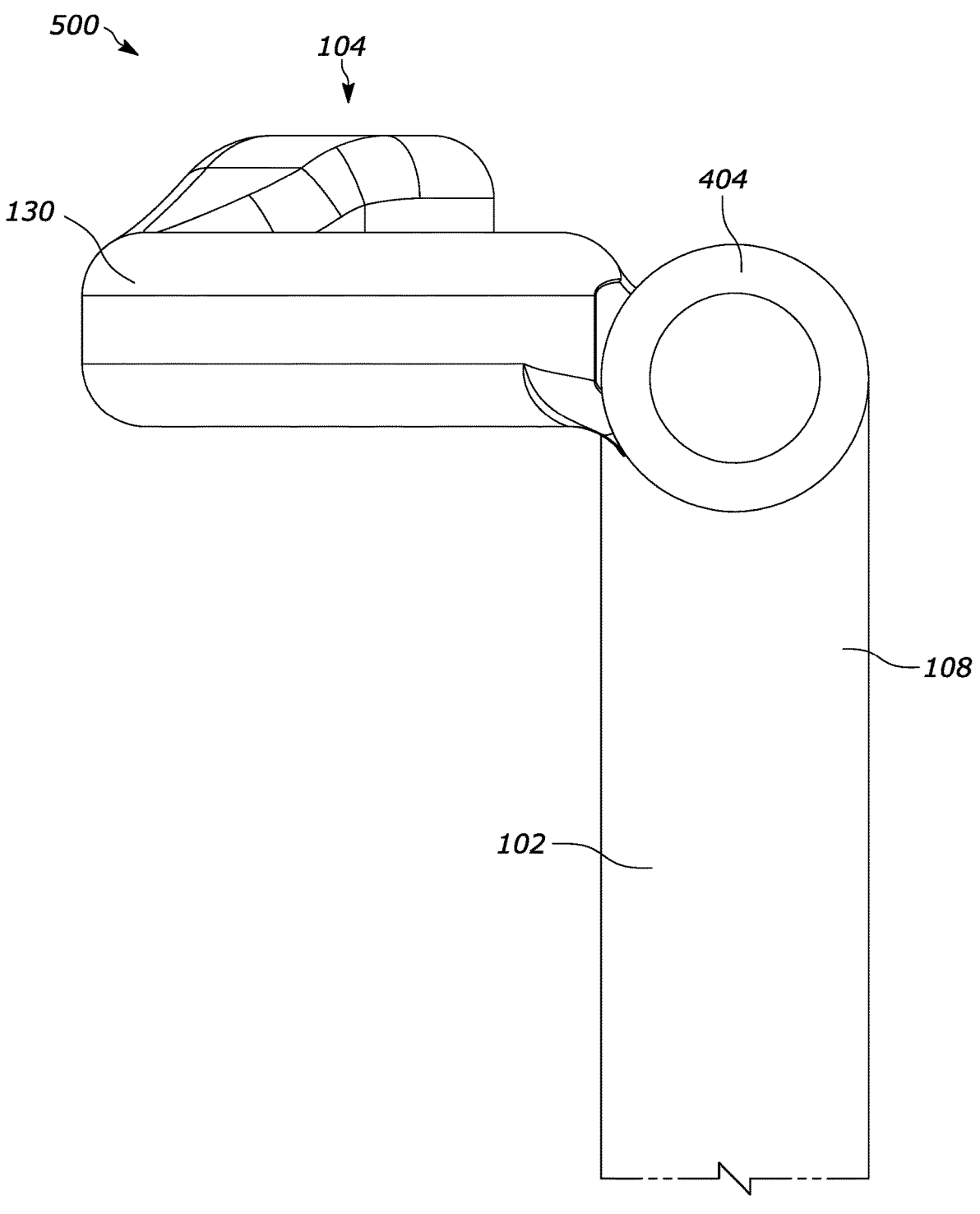

FIG. 7B is an enlarged isometric view of the proximal end of the nasopharyngeal airway device of FIG. 7A.

Figure 7C:
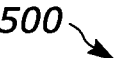
Figure 7C:
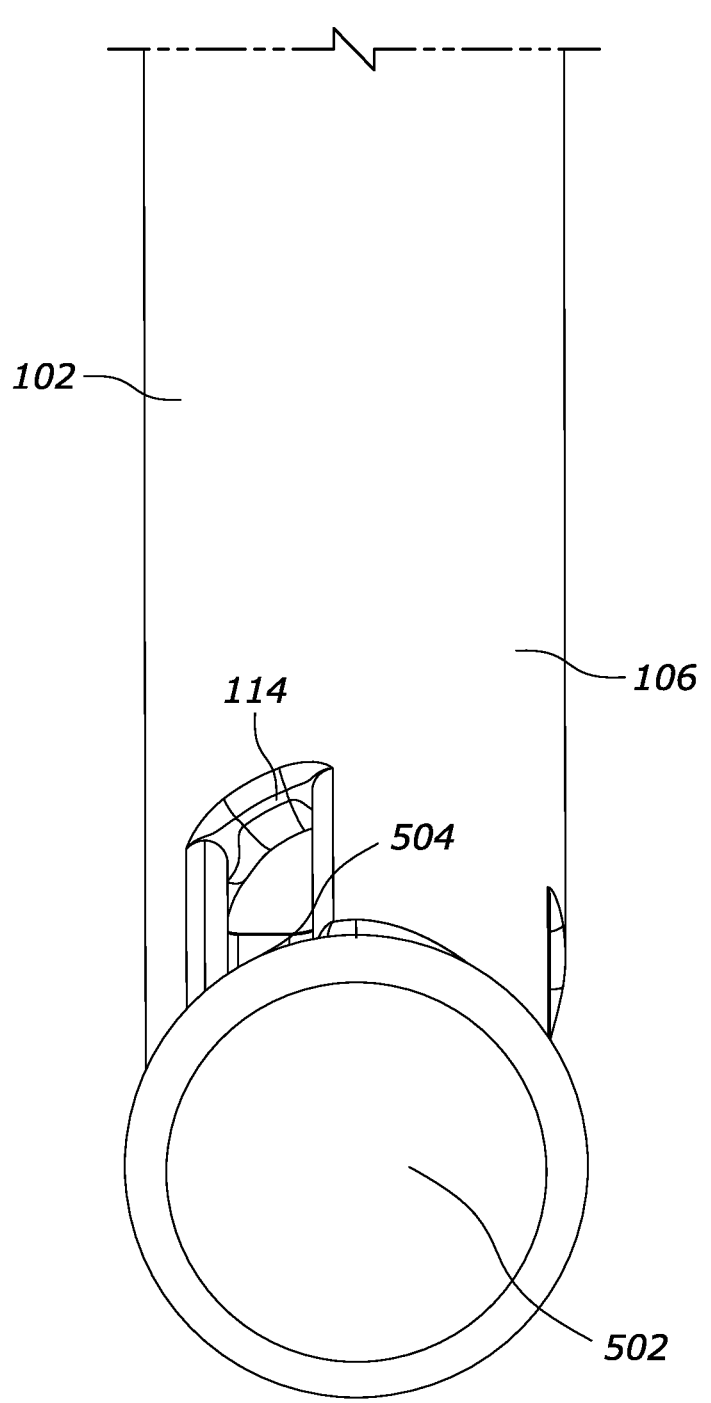

FIG. 7C is an enlarged isometric view of the distal end of the nasopharyngeal airway device of FIG. 7A.

Figure 8:
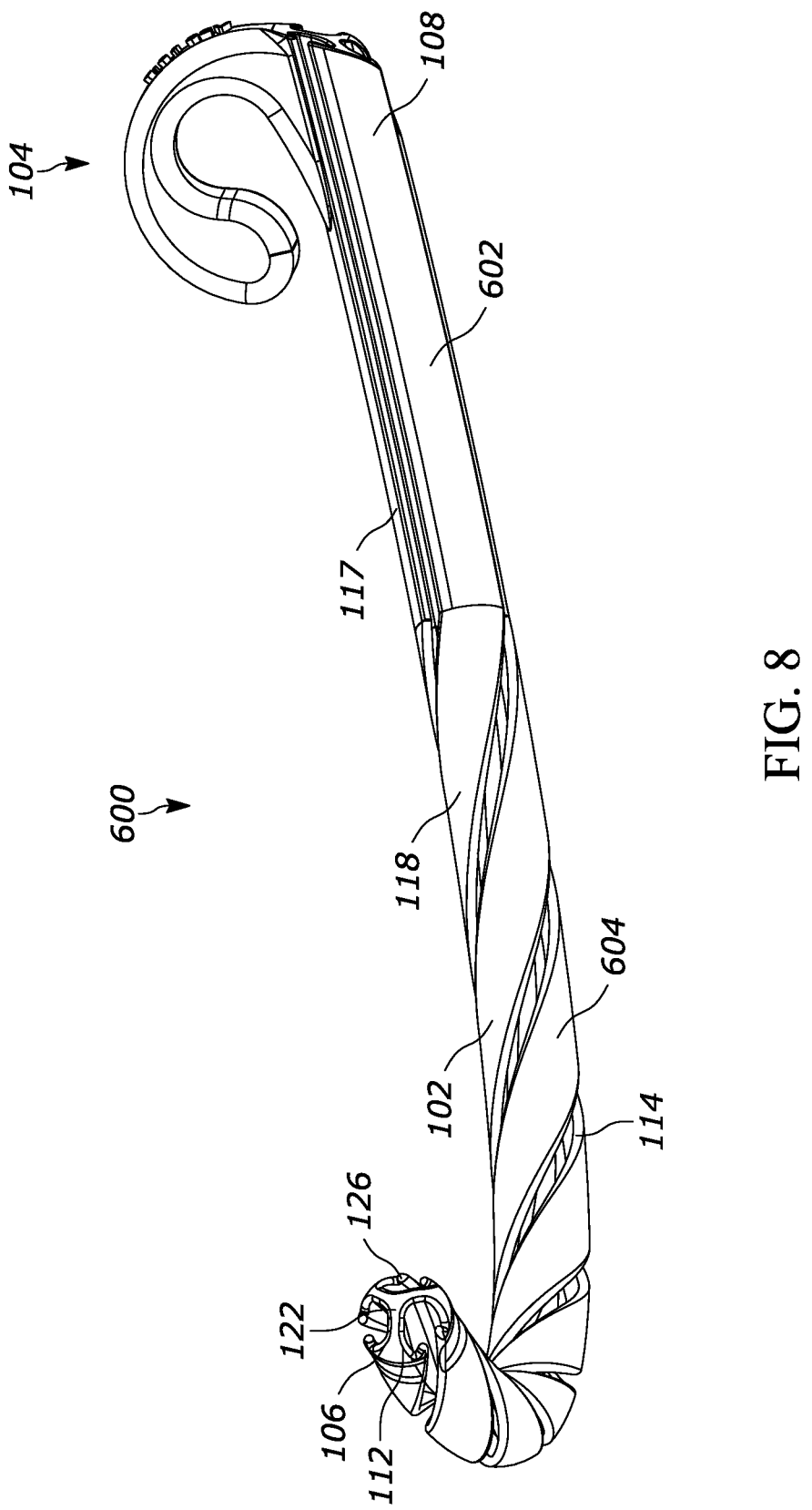

FIG. 8 is an isometric view of another nasopharyngeal airway device in accordance with a sixth example of the present disclosure.

Figure 9A:
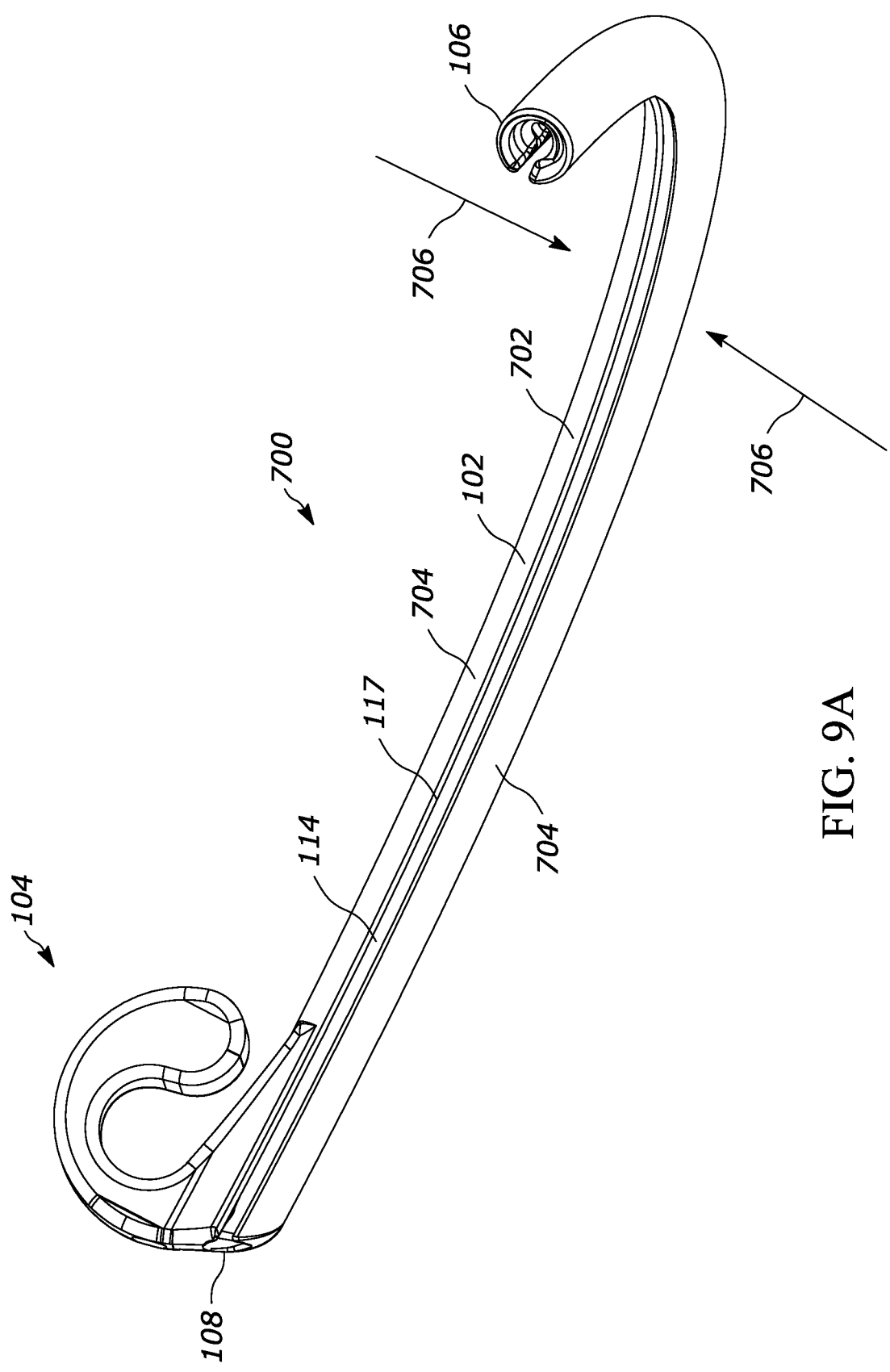

FIG. 9A is an isometric view of another nasopharyngeal airway device in accordance with a seventh example of the present disclosure.

Figure 9B:
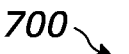

FIG. 9B is an isometric end-view of the distal end of the nasopharyngeal airway device of FIG. 9A.

Figure 10:
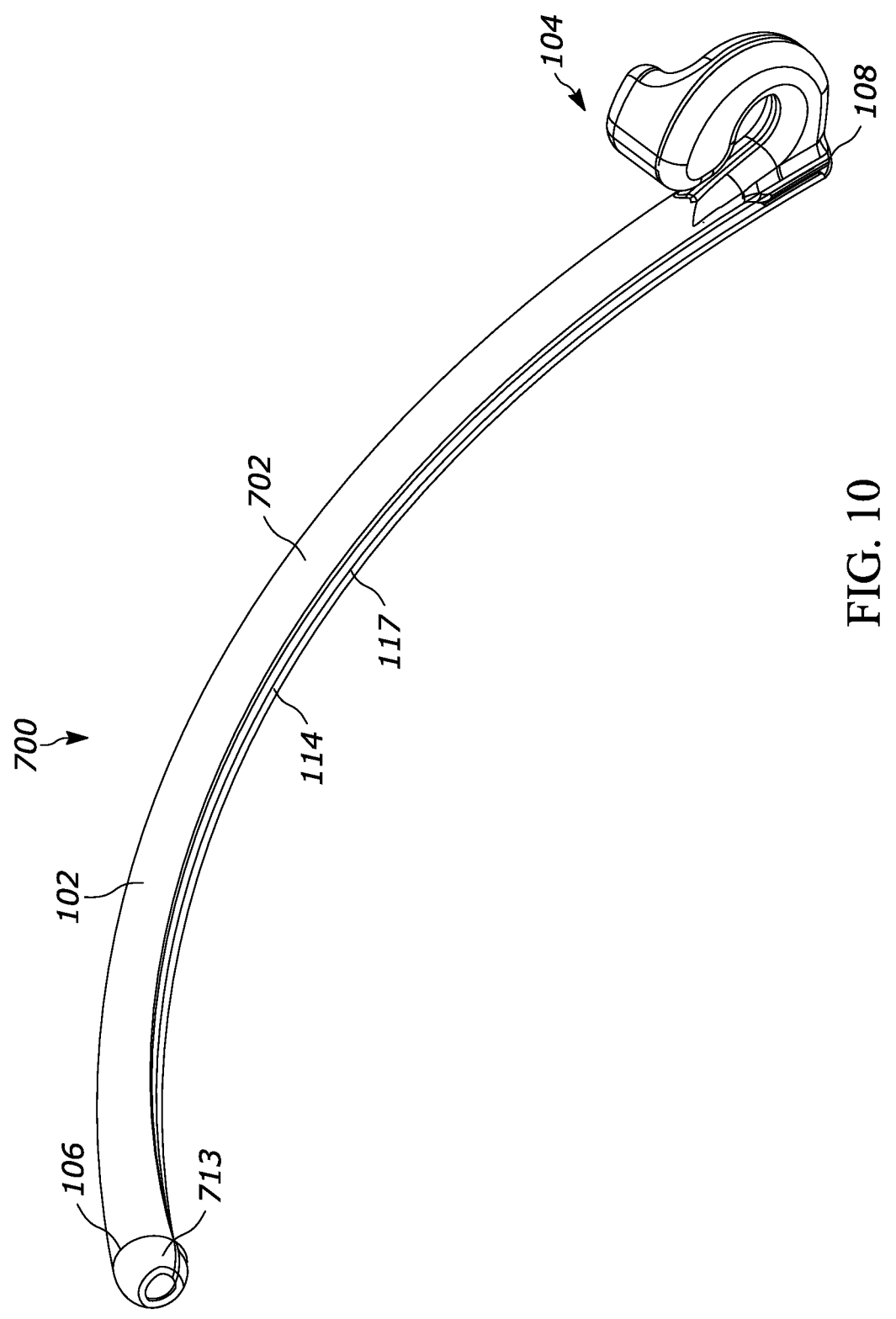

FIG. 10 is an isometric view of another implementation of the nasopharyngeal airway device of FIGS. 9A and 9B.

Figure 11:
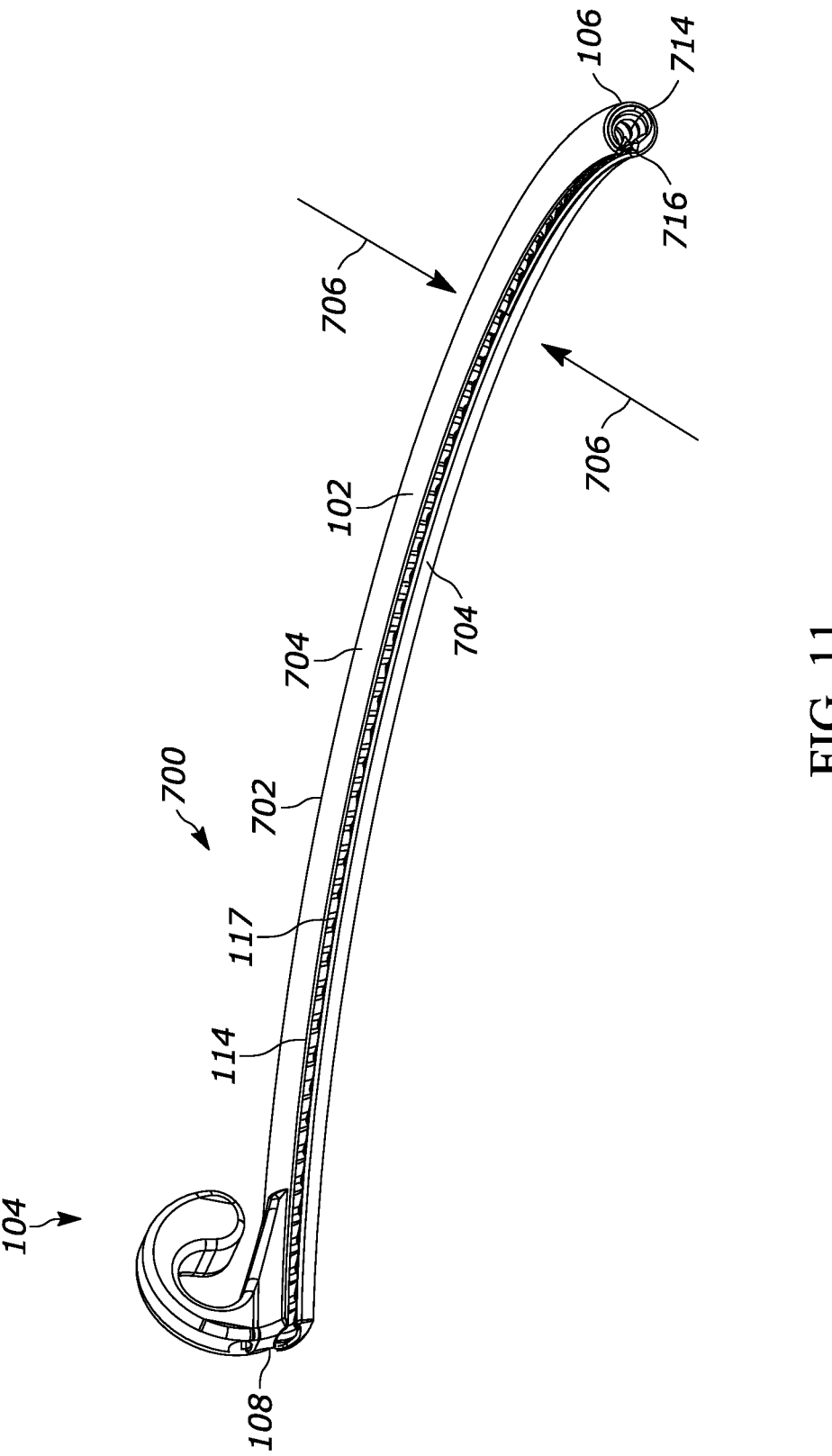

FIG. 11 is an isometric view of another implementation of the nasopharyngeal airway device of FIGS. 9A and 9B.

Figure 12:
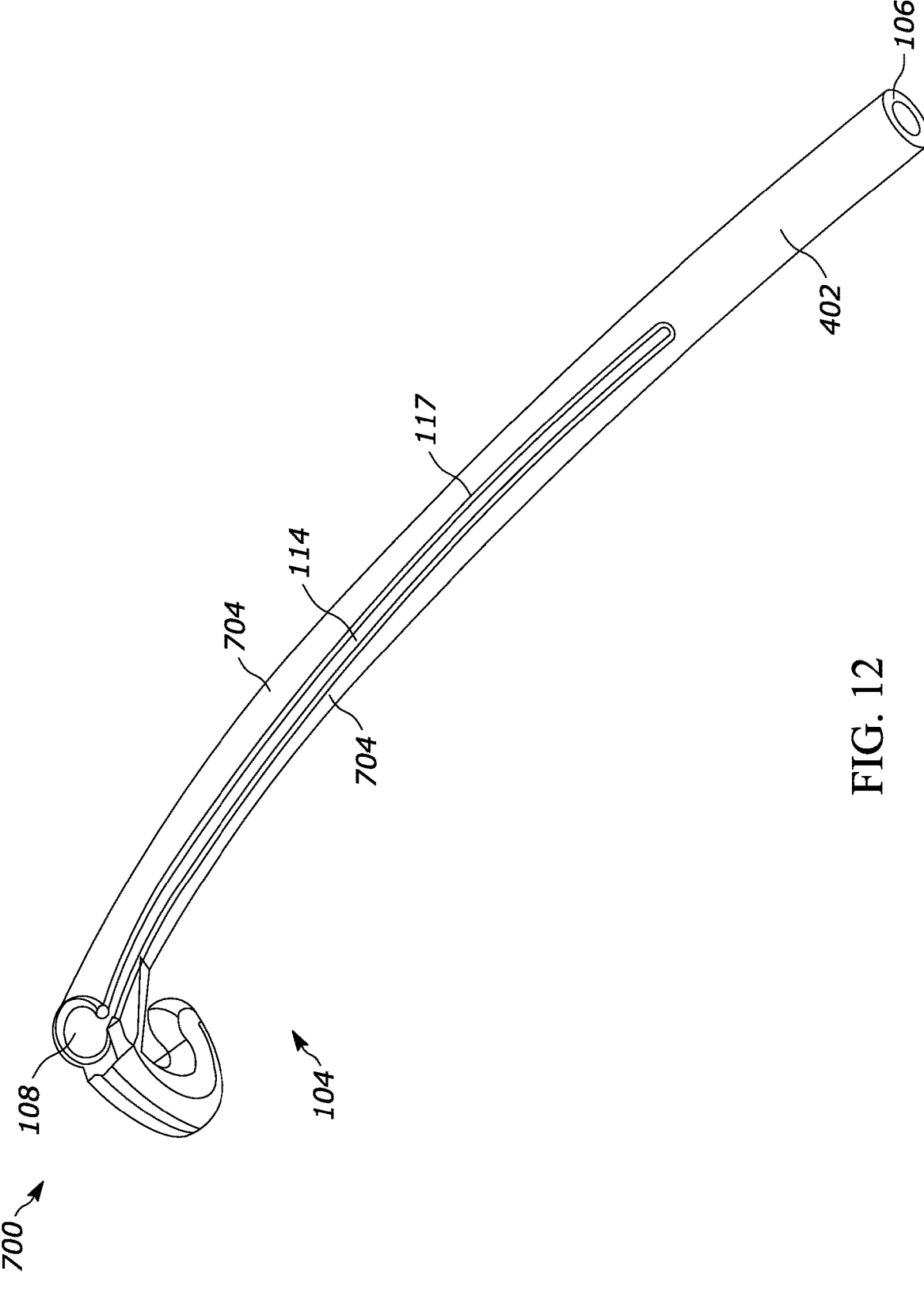

FIG. 12 is an isometric view of another implementation of the nasopharyngeal airway device of FIGS. 9A and 9B.

Figure 13:
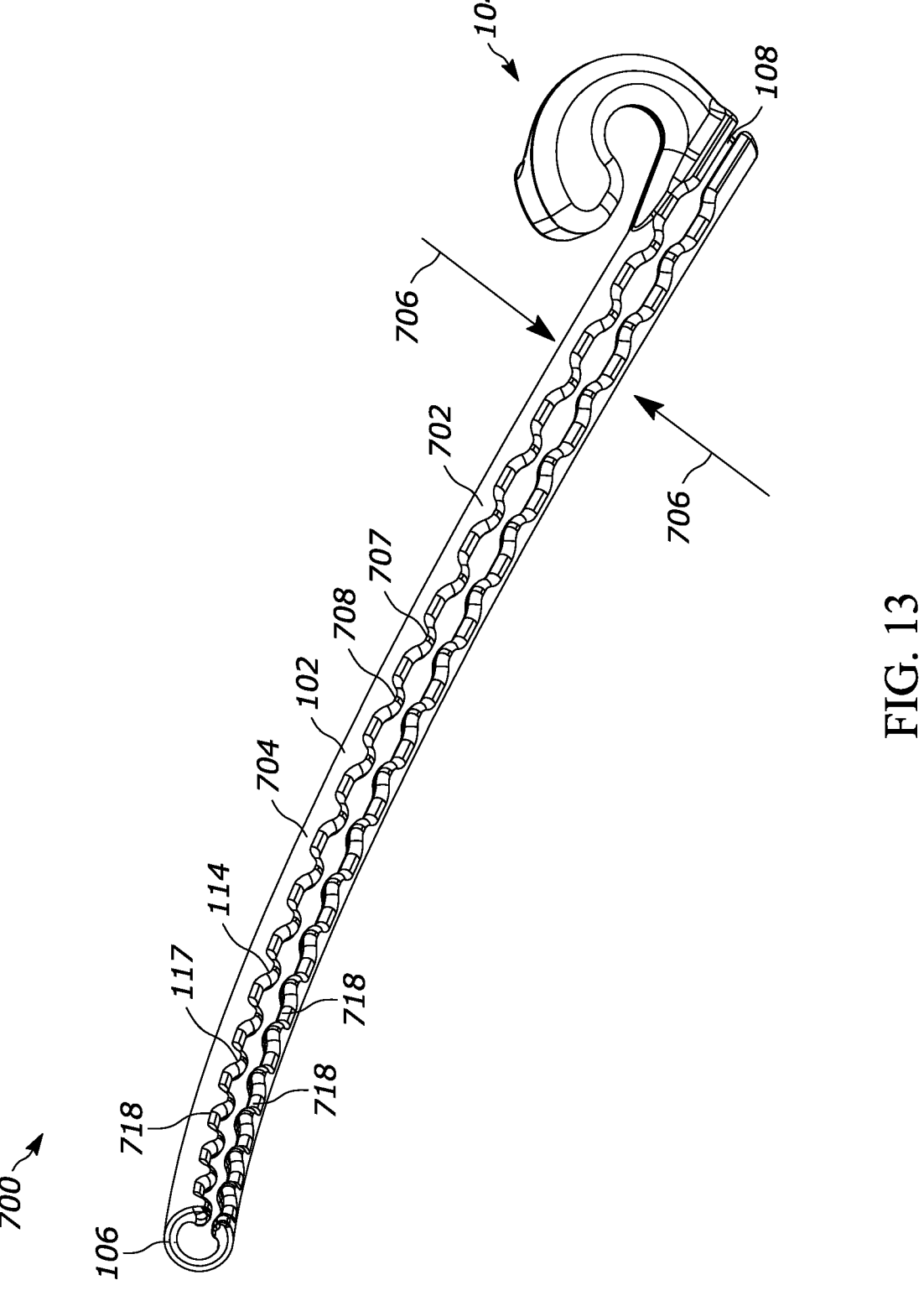

FIG. 13 is an isometric view of another implementation of the nasopharyngeal airway device of FIGS. 9A and 9B.

Figure 14:
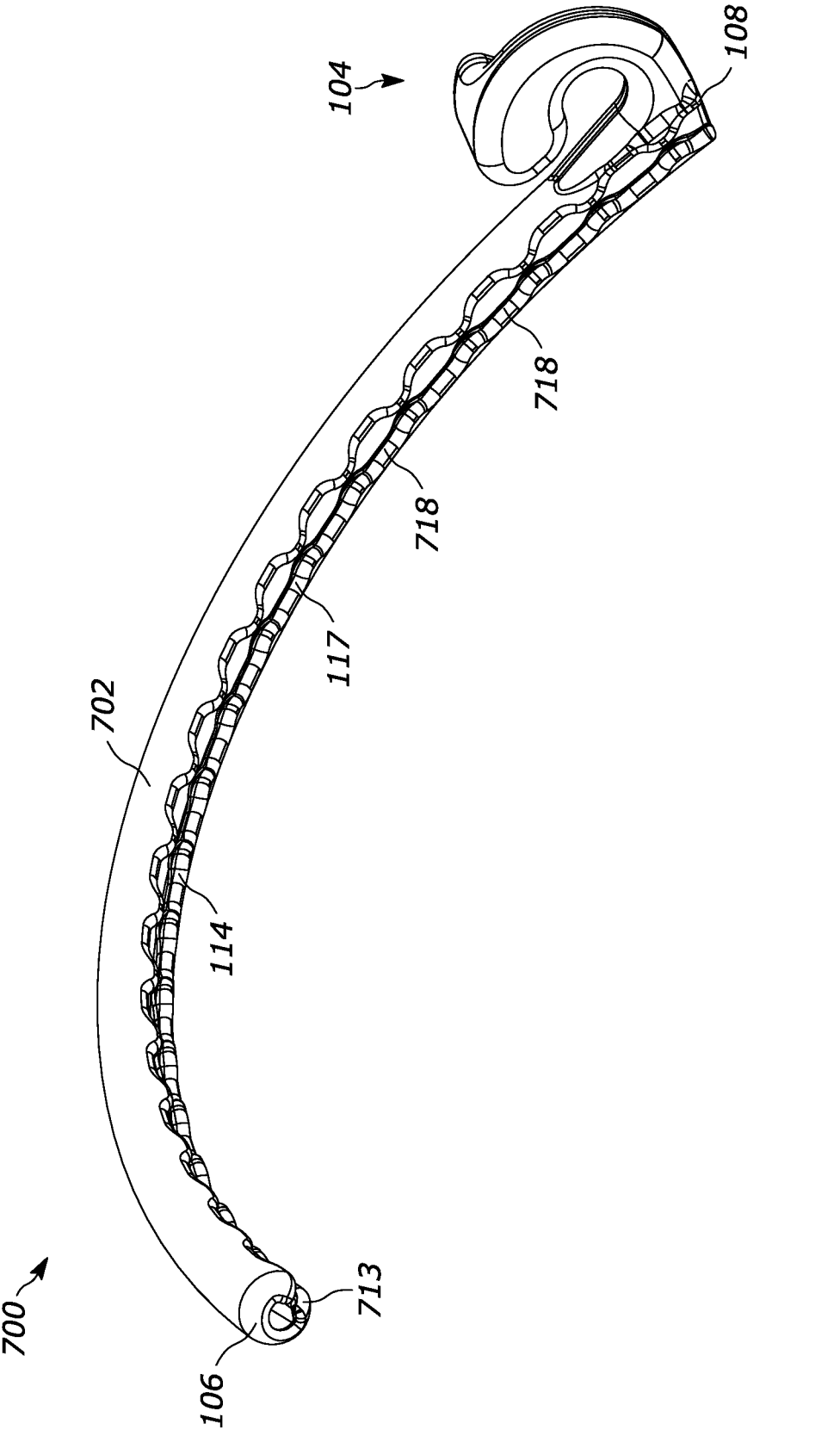

FIG. 14 is an isometric view of another implementation of the nasopharyngeal airway device of FIGS. 9A and 9B.

Figure 15:
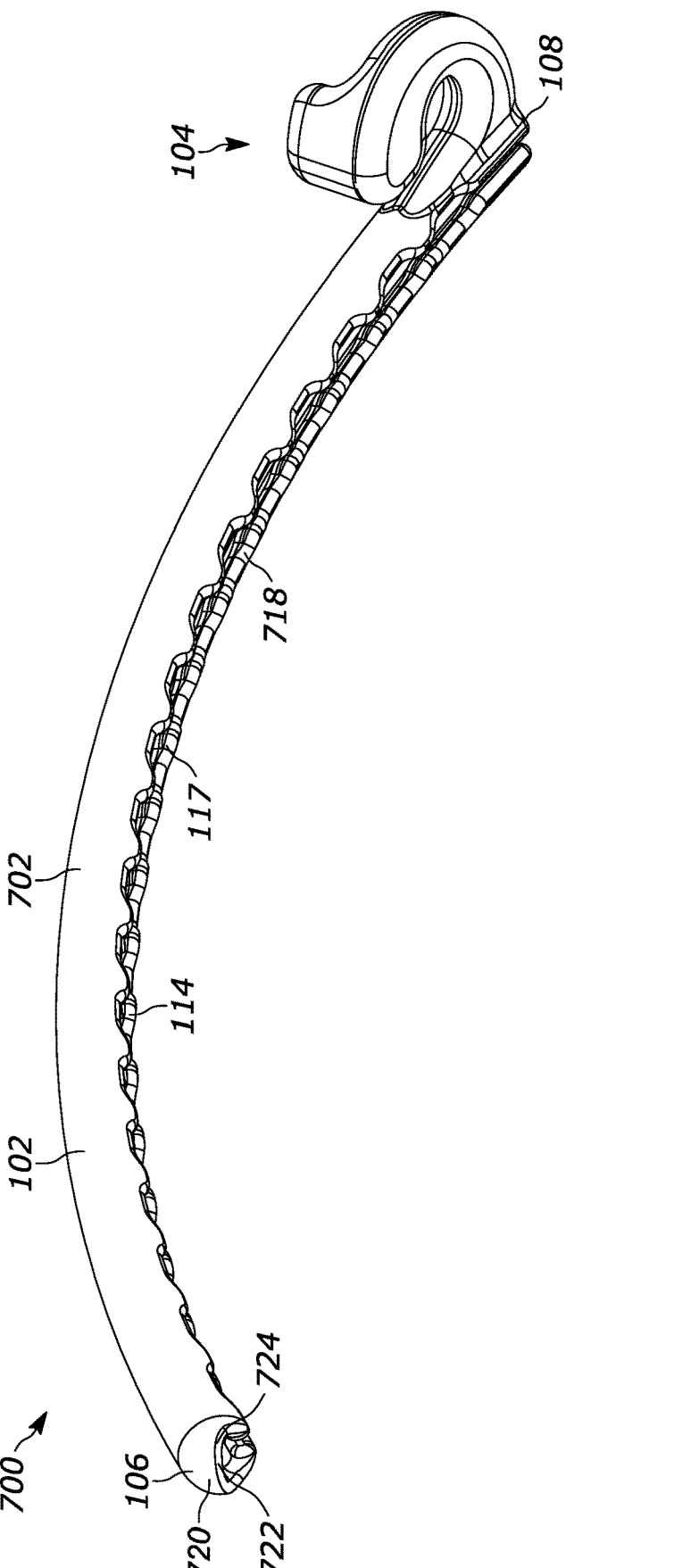

FIG. 15 is an isometric view of another implementation of the nasopharyngeal airway device of FIGS. 9A and 9B.

Figure 16:
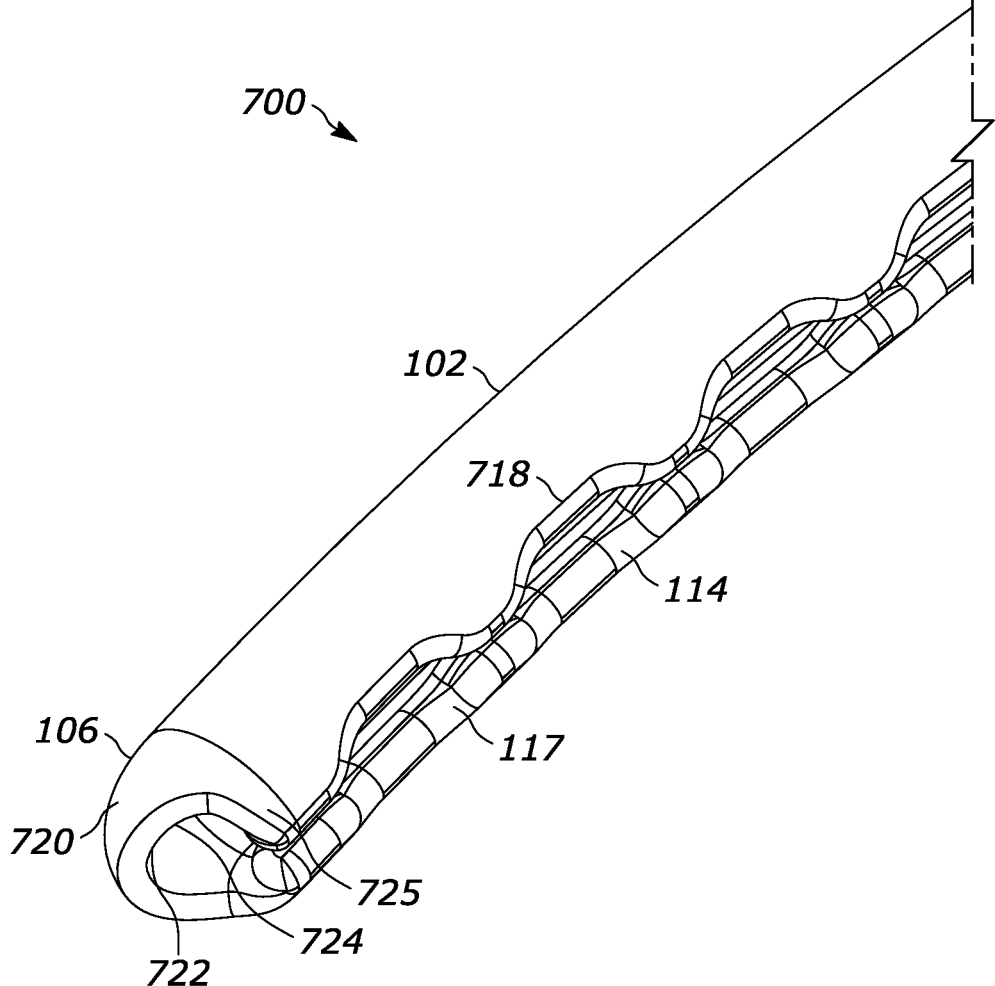

FIG. 16 is an isometric detailed view of another implementation of the nasopharyngeal airway device of FIGS. 9A and 9B.

Figure 17A:
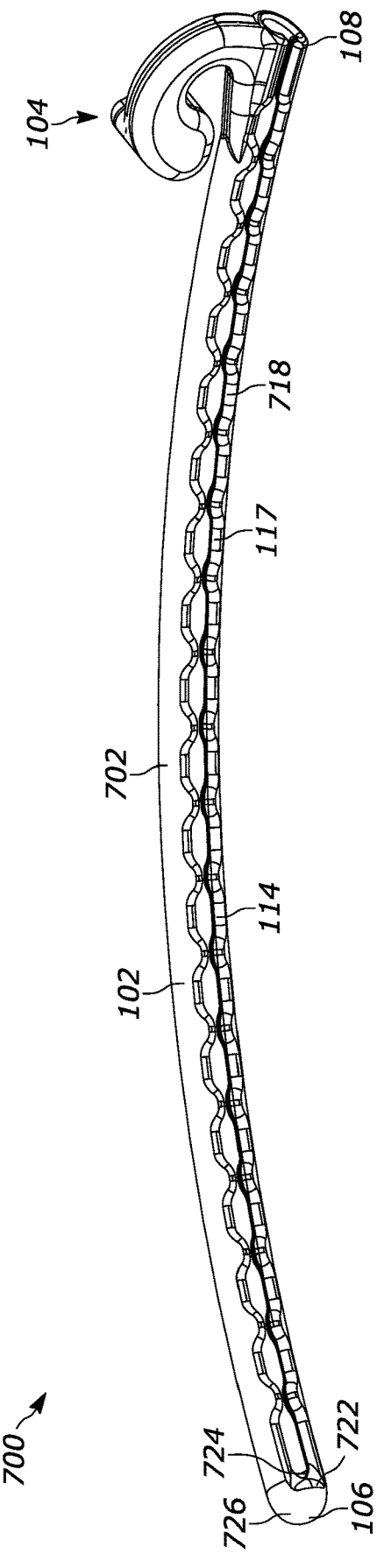

FIG. 17A is an isometric view of another implementation of the nasopharyngeal airway device of FIGS. 9A and 9B.

Figure 17B:
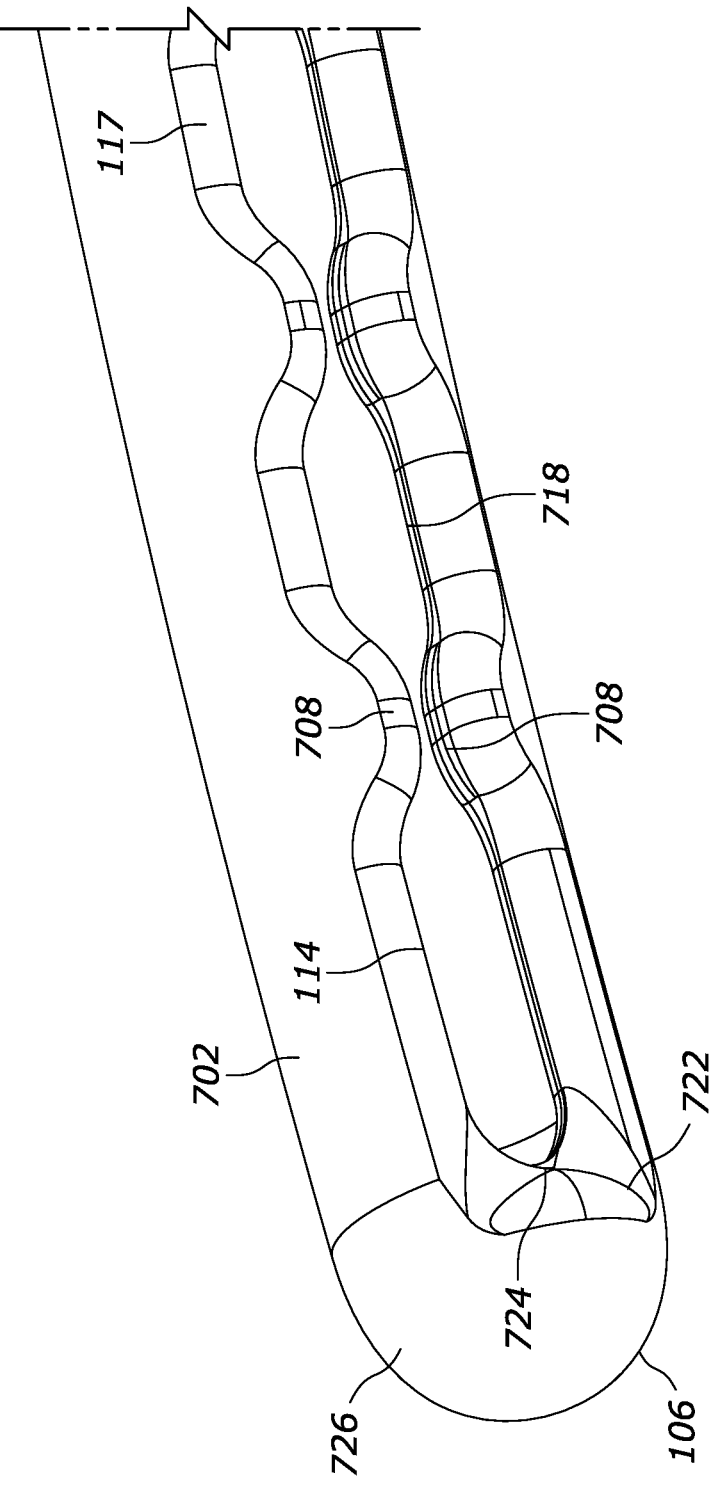

FIG. 17B is an isometric detailed view of the nasopharyngeal airway device of FIG. 17A showing the fully closed rounded end.

Figure 18:
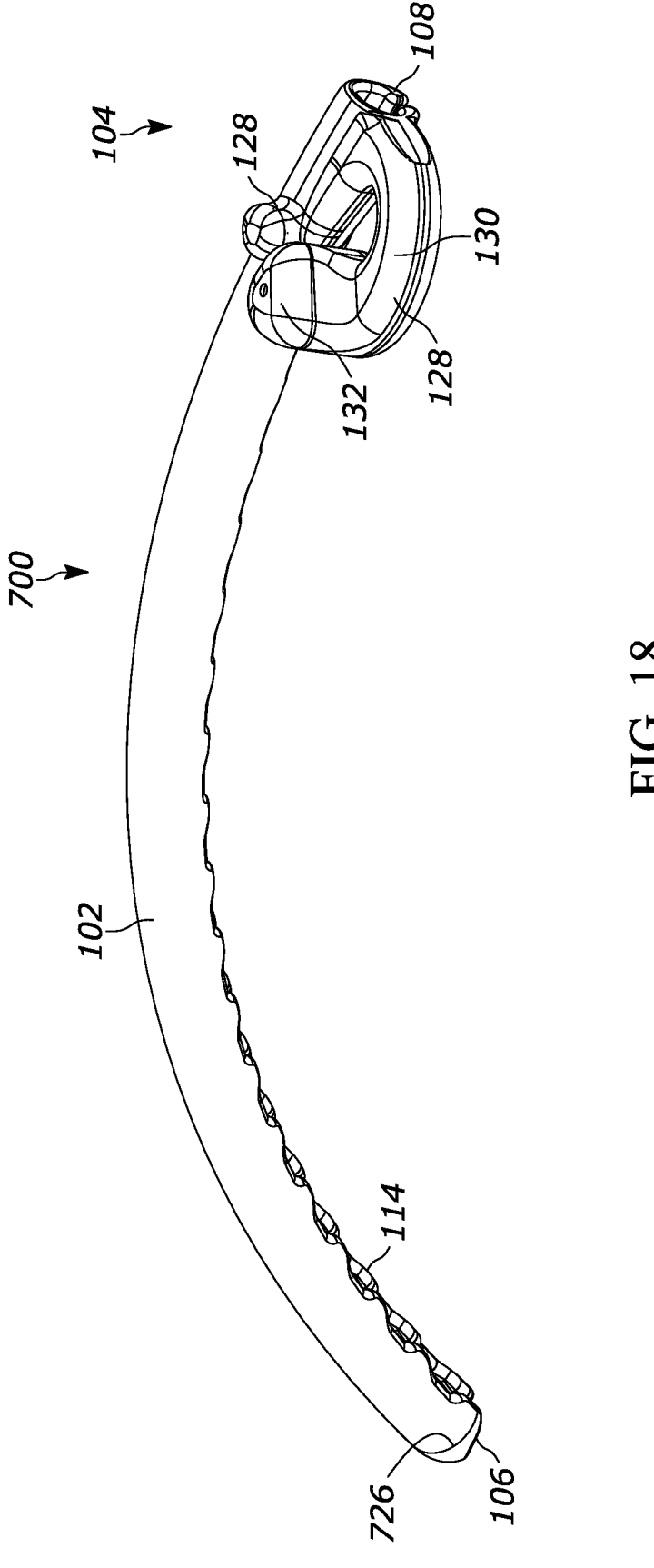

FIG. 18 is an isometric view of another implementation of the nasopharyngeal airway device of FIGS. 9A and 9B.

DETAILED DESCRIPTION

Although the following text discloses a detailed description of example methods, apparatus and/or articles of manufacture, it should be understood that the legal scope of the property right is defined by the words of the claims set forth at the end of this patent. Accordingly, the following detailed description is to be construed as examples only and does not describe every possible example, as describing every possible example would be impractical, if not impossible. Numerous alternative examples could be implemented, using either current technology or technology developed after the filing date of this patent. It is envisioned that such alternative examples would still fall within the scope of the claims.

Figure 1A:
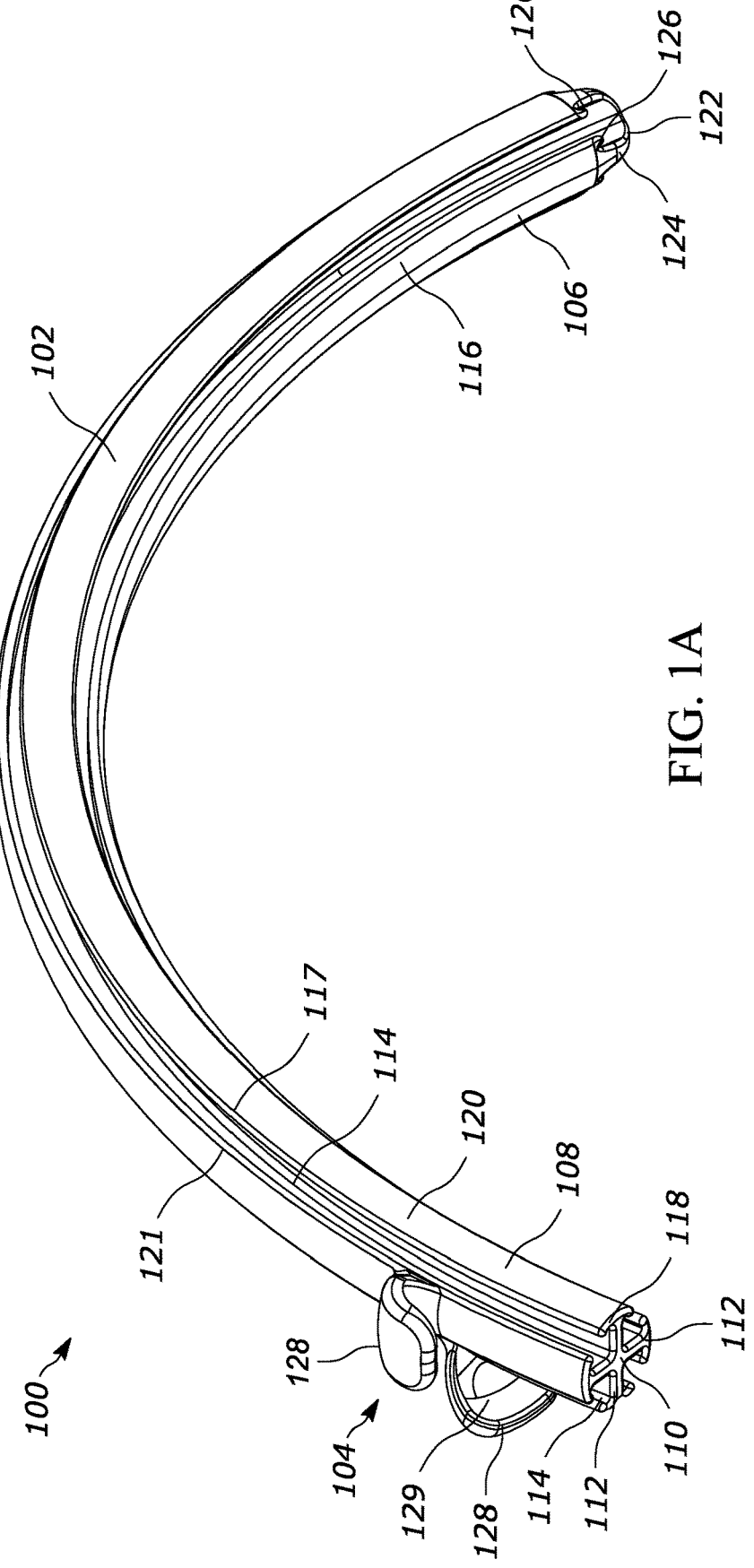
FIG. 1A is an isometric view of a nasopharyngeal airway device in accordance with a first example of the present disclosure.

FIG. 1A is an isometric view of a nasopharyngeal airway device 100 in accordance with a first example of the present disclosure. The nasopharyngeal airway device 100 may be used for air-way patency through the nose. In some examples, the nasopharyngeal airway device 100 is adapted to be worn the entire night while an individual is sleeping to prevent or reduce upper airway obstruction. Thus, the nasopharyngeal airway device 100 may be helpful to treat sleep apnea. The nasopharyngeal airway device 100 may be worn while the individual is awake. For example, the nasopharyngeal airway device 100 may be helpful to assist breathings of children or other individuals with severe facial abnormalities and/or hypotonia.

In the example shown, the nasopharyngeal airway device 100 includes an elongate body 102 and a securement component 104. The elongate body 102 may be referred to as a fluted body or an open-channel body. The elongate body 102 may have a general curvature to aid in the insertion of the elongate body 102 into the nose of the individual. The securement component 104 may be referred to as a fixation device or a fastener. The securement component 104 may be configured to secure the nasopharyngeal airway device 100 within a nostril of an individual. In some implementations, the securement component 104 is self-supporting and has a low profile that is contoured to the opening of the nostril to deter the nasopharyngeal airway device 100 from being inadvertently removed when worn. Moreover, in some implementations, the securement component 104 is sized and/or structured to deter the nasopharyngeal airway device 100 from being inserted into the nasal cavity beyond a threshold amount. In some implementations, the securement component 104 can include one or more surface indentations, protrusions, adhesive, and/or another structure that provides friction to further secure the nasopharyngeal airway device 100 within the nostril of the individual. While the nasopharyngeal airway device 100 includes one elongate body 102, a pair of elongate bodies 102 (one to be received in each nostril) may be provided (see, for example, FIGS. 4A and 4B).

The elongate body 102 has a distal end 106 and a proximal end 108. A length of the elongate body may be patient specific but may generally extend between approximately 7 centimeters (cm) and approximately 17 cm and/or between approximately 5 cm and approximately 16 cm. However, the elongate body 102 may have different lengths, as appropriate, such as for neonatal, pediatric, adolescent, and adult use. An overall diameter of the elongate body 102 may be between approximately 3 mm and approximately 8 mm. However, the overall diameter of the elongate body 102 may be a different dimension (e.g., 8.2 mm, 9.0 mm). Additionally, the elongate body 102 may have an oblong or cross-section other than one that is substantially circular. In other implementations, a first portion of the elongate body 102 may have a first diameter or thickness and a second portion of the elongate body 102 may have a second diameter or thickness. In such implementations, the second portion may be sized to secure the elongate body 102 within the nostril of the individual and/or may be formed as a nasal trumpet.

The nasopharyngeal airway device 100 including the elongate body 102 may be made from a medical grade silicone elastomer with Shore A hardness of between approximately 30 A and approximately 65 A. As another example, the nasopharyngeal airway device 100 including the elongate body 102 may be made from a medical grade silicone elastomer with Shore A hardness of between approximately 10 A and approximately 70 A. Thus, the nasopharyngeal airway device 100 and the elongate body 102 may be relatively flexible and may be relatively easy to insert into the nostril/nasal cavity of the individual. Other materials and/or harnesses may be used.

For example, the nasopharyngeal airway device 100 or any of the disclosed examples may be made of silicone, thermoplastic elastomer, PVC and may be produced using any technique such as injection molding, forming, three-dimensional (3D) printing, bonding multiple components together, and/or extrusion techniques. In some implementations, the proximal end 108 is a stiffer material such as Polyvinyl chloride (PVC) and the distal end 108 may be a softer material such as silicone.

The elongate body 102 has a hub 110 and a plurality of ribs 112. The ribs 112 may be referred to as self-supporting members or radial walls. The ribs 112 may serve as a stent or prop that opens and/or provides airways through the elongate body 102.

The ribs 112 outwardly extend from the hub 110. In the example shown, the ribs 112 are positioned at approximately 90° relative to one another. However, the ribs 112 may be differently positioned and/or more or fewer ribs 112 may be provided. As an example, if three ribs 112 are provided instead of four, the ribs 112 may be positioned at approximately 120° relative to one another.

In the example illustrated, the ribs 112 extend longitudinally along at least half of the elongate body 102. Thus, the ribs 112 extend along the elongate body 102 from the proximal end 108 of the elongate body 102 to a location beyond a midpoint of the elongate body 102. However, the ribs may alternatively extend along only a portion of the elongate body 102. For example, the ribs 112 may be arranged between the distal end 106 and the proximal end 108 or the ribs 112 may be arranged from the proximal end 108 to a location before the midpoint of the elongate body 102. The ribs 112 may alternatively be arranged from the distal end 106 to a location before the midpoint of the elongate body 102 or another portion on the elongate body 102. In such examples, the distal end 106 may include a tubular portion (see, for example, FIGS. 6A and 7A). If the tubular portion is included, a transition portion may be included where the ribs 112 transition to the tubular portion. The hub 110 and the ribs 112 may not be included in the tubular portion. Thus, the elongate body 102 may include one or more tubeless airway portions where the hub 110 and the ribs 112 are provided and the elongate body 102 may include one or more tubular portions where the hub 110 and the ribs may or may not be provided.

Channels 114 are defined between the ribs 112. The channels 114 may be referred to as ruts, grooves, depressions, and/or flow paths. The nasopharyngeal airway device 100 illustrated in FIG. 1A includes four channels 114. However, one or more channels 114 may be defined between the ribs 112 such as, for example, two channels, three channels, five channels, etc. The channels 114 may be D-shaped, C-shaped, circular, or have any other suitable cross-section.

The one or more channels 114 extend along the elongate body 102. In the example shown, the channels 114 extend straight through a length of the nasopharyngeal airway device 100. Alternatively, the channels 114 may rotate/twist down at least part of the length of the nasopharyngeal airway device 100, such as in a toroidal configuration and/or the implementation shown in FIG. 8. Having the channels 114 twist may make the nasopharyngeal airway device 100 more comfortable for an individual to wear.

The elongate body 102 may have an outer surface 116 that defines the channels 114. The outer surface 116 may be referred to as an exterior surface.

In the example shown, the channels 114 extend from the distal end 106 of the elongate body 102 to the proximal end 108 of the elongate body 102. The channels 114 may extend throughout a majority of the nasopharyngeal airway device 100. Thus, the one or more open channels 114 may extend longitudinally along at least half of the elongate body 102. Put another way, the one or more of the channels 114 extend along the elongate body 102 from the proximal end 108 to a location beyond a midpoint of the elongate body 102. In other examples, the channels 114 may not extend beyond the midpoint of the elongate body 102.

Each channel 114 has a lateral opening 117. The lateral openings 117 extend longitudinally between the distal end 106 and the proximal end 108. The lateral openings 117 are defined between corresponding ribs 112. In the example shown, the lateral openings 117 are contiguous between the distal end 106 and the proximal end 108. The channels 114 include the tubeless airway portions. As an alternative, one or more of the lateral openings 117 may be divided into sub-lateral openings by portions of the elongate body 102. The sub-lateral openings may be intermittently spaced and may extend longitudinally along the elongate body 102.

In the example shown, because the lateral openings 117 are open to the exterior of the nasopharyngeal airway device 100, air can enter and exit the nasopharyngeal airway device 100 along a portion, the majority, or the entire length of the elongate body 102. The lateral openings 117 may allow access within the channels 114 to more-easily clean the nasopharyngeal airway device 100. For example, any mucus or buildup within the channels 114 may be removed by irrigating the lateral openings 117.

The lateral openings 117 may also be adapted to prevent air only flowing through the distal end 106 in a manner that causes the individual using the nasopharyngeal airway device 100 to have a sore throat. By allowing air to flow through the lateral openings 117 along a majority of the elongate body 102, air flowing through the elongate body 102 may be more dispersed and, thus, less concentrated on a particular location on the individual. As another example, by allowing air to flow through the lateral openings 117 along at least a portion of the elongate body 102 (e.g., at the distal end 106), air flowing through the elongate body 102 may be more dispersed and, thus, less concentrated on a particular location on the individual.

In the example shown, each rib 112 includes a distal flange 118. The lateral openings 117 are shown being defined between adjacent flanges 118. In an alternative example, the ribs 112 may not include the flanges 118 or the flanges 118 may be differently configured. For example, the ribs 112 and the flanges 118 may form an L-shape instead of the T-shape illustrated in FIG. 1A.

The flanges 118 preferably have an arced outer face 120. The flanges 118 also include curved/rounded sides 121. The cross-section of the channels 114 includes an approximately 90° corner provided by the ribs 112 and a curved portion provided by the distal flanges 118. Other cross-sections of the channels 114 may be provided.

The arced outer face 120 may have a smooth exterior. Providing the arced outer face 120 with a smooth exterior may facilitate atraumatic insertion of the elongate body 102 into the nasal cavity. The arced outer face 120 and/or the channels 114 may include a surface texture and/or a coating.

The coating may be a lubricious coating (e.g., a water-based lubricant) that includes, for example, a local anesthetic coating such as Lidocaine. In implementations where a lubricant and/or a local anesthetic are provided, the nasopharyngeal airway device 100 may be packaged in a foil pouch or in another fluid-resistant packaging. Alternatively, the nasopharyngeal airway device 100 may be packaged in, for example, a Tyvek pouch, and the lubricant and/or the local anesthetic may be provided separately.

The coating may also be a hydrophobic coating and/or a hydrophilic coating. The surface texture and/or the coating may prevent mucus buildup and may further reduce the chances of the elongate body 102 clogging. Providing the nasopharyngeal airway device 100 with the lateral openings 117 instead of providing a closed channel (not shown) can serve to reduce the chances that the channels 114 become clogged with mucus. For example, should mucus accumulate in a portion of one of the channels 114, air may circumvent the obstructed channel via, for example, the lateral opening 117.

Figure 1B:
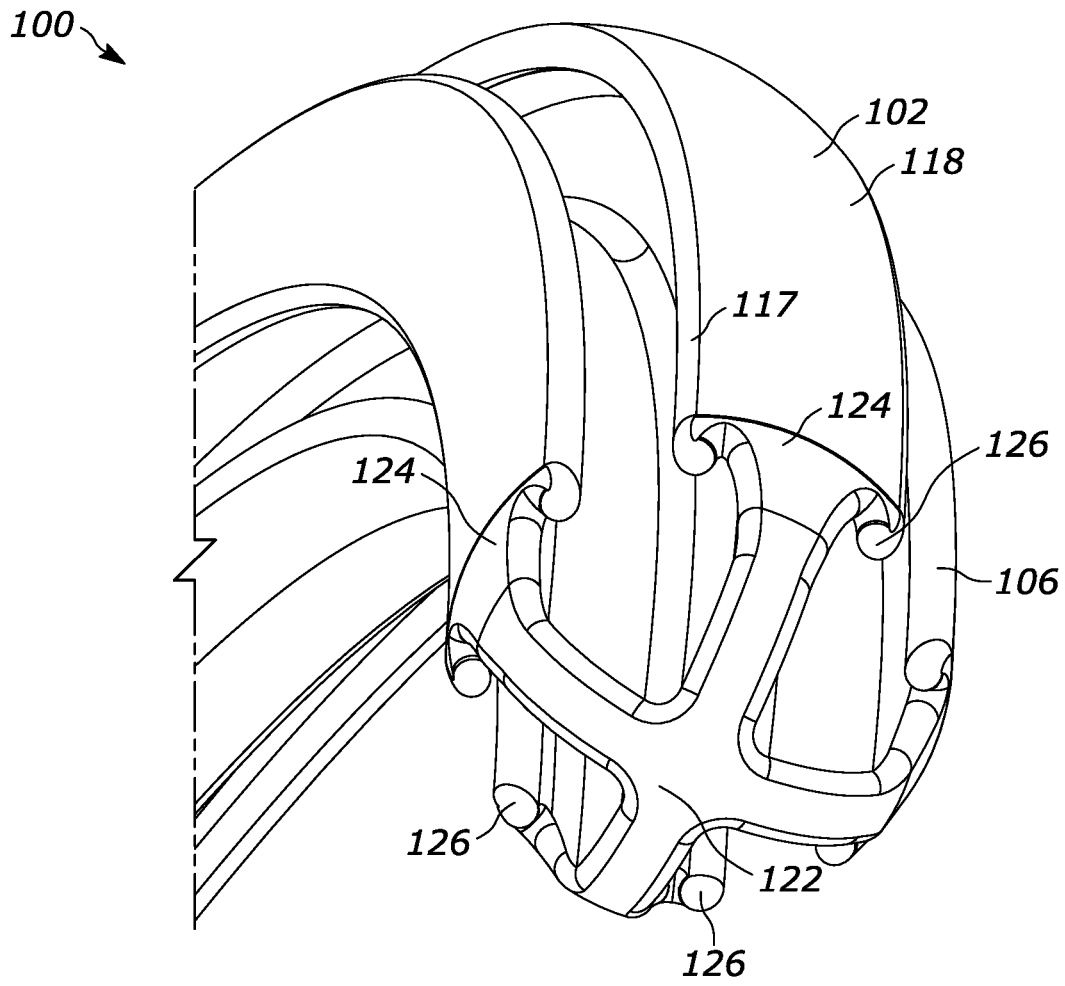
FIG. 1B is an enlarged isometric view of a distal end of the nasopharyngeal airway device 100 of FIG. 1A.

FIG. 1B is an enlarged isometric view of the distal end 106 of the nasopharyngeal airway device 100 of FIG. 1A. The distal end 106 of the elongate body 102 has a rounded portion 122. The rounded portion 122 may be adapted to allow the elongate body 102 to be more easily inserted into the nostril and the nasal cavity.

In the example shown, the rounded portion 122 of the elongate body 102 includes inwardly-curved triangular portions 124 that form the rounded portion 122 at the distal end 106 of the elongate body 102. The triangular portions 124 are defined by the flanges 118. The rounded portion 122 is substantially symmetric across the X-axis of the elongate body 102 and across the Z-axis of the elongate body 102. In another example, the distal end 106 may have a different contour. For example, the distal end 106 may alternatively be beveled, tapered, or may have any other contour to help ease insertion of the elongate body 102 into/through the nose.

The distal end 106 also includes surface tension reducing protrusions 126. The protrusions 126 are positioned on each side of the triangular portion 124 at the distal end 106. The protrusions 126 may be adapted to reduce surface tension of mucus that may attempt to accumulate at the distal end 106 of the elongate body 102. Thus, the protrusions 126 may prevent mucus buildup and further reduce the chances of the nasopharyngeal airway device 100 clogging.

Referring back to FIG. 1A, the securement component 104 is securely coupled to the elongate body 102. The securement component 104 is shown being coupled adjacent the proximal end 108. In another example, the nasopharyngeal airway device 100 may be attached to a relatively long hose used to deliver oxygen or another gas to an individual. In such an example, the securement component 104 may not be considered to be coupled to the proximal end 108. In the example shown, the securement component 104 includes a pair of projections 128. Preferably, the projections 128 are integral to the elongate body 102. However, the projections 128 may alternatively be attached to the elongate body 102 in any suitable way. The projections 128 are positioned outside of the dimensional envelope of the elongate body 102 and extend away from a tangential plane that intersects the outer surface 116 of the elongate body 102.

Alternatively, one projection 128 or more than two projections 128 may be included. While the projections 128 are shown positioned approximately 90° from one another, the projections 128 may alternatively be positioned on opposite sides of the elongate body 102.

In the example shown, the projections 128 are fins 129 that extend toward the proximal end 108 of the elongate body 102. In some examples, the fin 129 disposed on the left side of the elongate body 102 as shown in FIG. 1A may extend rearward farther than the fin 129 disposed on the top of the elongate body 102 as shown in FIG. 1A. However, the fins 129 may be differently arranged.

The fins 129 are adapted to be inserted into the nostril and are further adapted to provide a biasing force to secure the nasopharyngeal airway device 100 within the nostril. For example, the fins 129 may provide a biasing force when the distal ends of the fins 129 are moved toward the outer surface 116 of the elongate body 102. The fins 129 are preferably petal shaped and curve rearwardly away from the distal end 106. However, the projection(s) 128 may take different forms and the fins 129 may have different shapes. For example, the projection 128 may be a clip that extends forward toward the distal end 106 (see, for example, FIG. 2A).

Figure 2A:
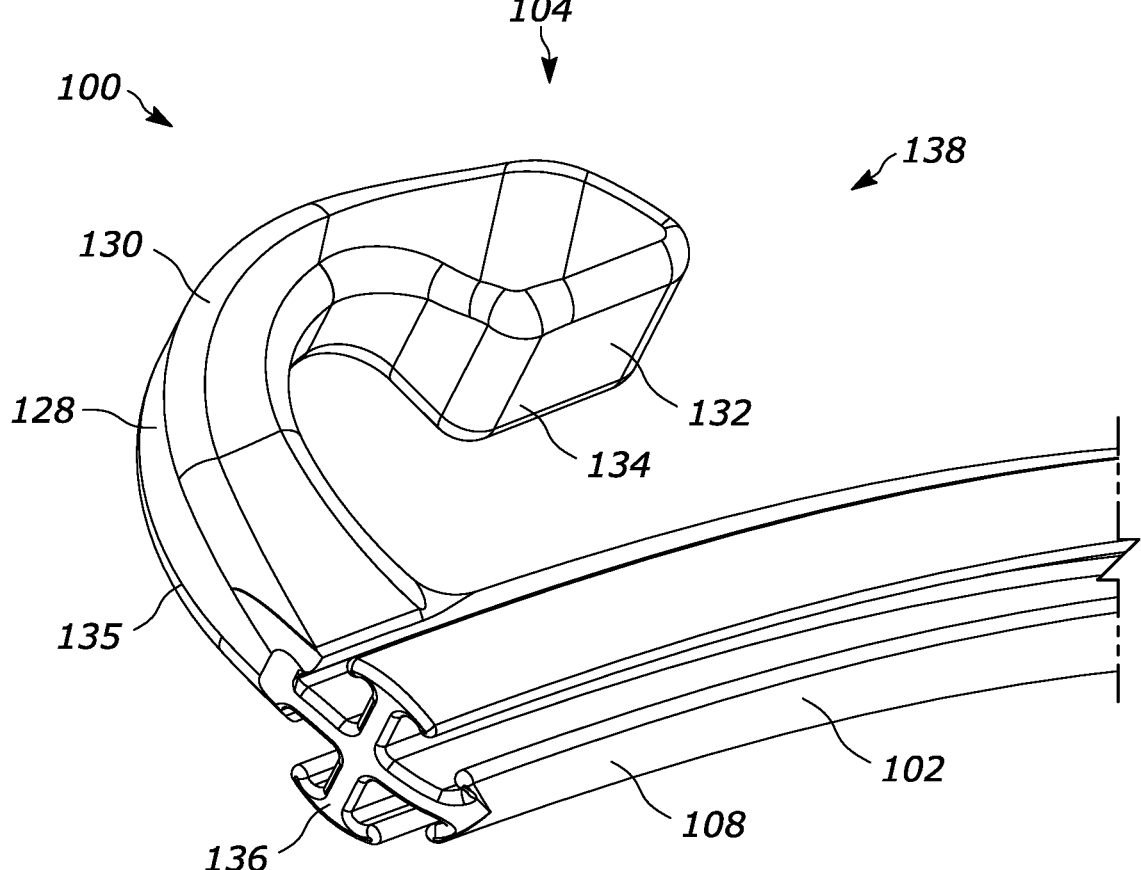
FIG. 2A is an enlarged isometric view of a proximal end of the nasopharyngeal airway device of FIG. 1A including an alternative securement component.

FIG. 2A is an enlarged isometric view of the proximal end 108 of the nasopharyngeal airway device 100 of FIG. 1A including an alternative securement component 104. In contrast to the fins 129 disclosed in FIG. 1A, the projection 128 of the securement component 104 of FIG. 2A includes an arced arm 130. The arced arm 130 includes a distal foot 132. The foot 132 includes a flat surface 134. The flat surface 134 may be arranged to engage the nasal septum of the individual after the elongate body 102 is inserted into the nose to secure the nasopharyngeal airway device 100 of FIG. 2A. In another example, the surface 134 may not be flat.

The arced arm 130 extends toward the distal end 106 of the elongate body 102 and has a proximal end that is securely coupled to the elongate body 102. In the example shown, an arm-outer surface 135 and a proximal-end outer surface 136 have a substantially similar radius. Thus, the curvature of the arced arm 130 and the curvature of the distal end 106 are similar. Providing the proximal-end outer surface 136 with the substantially similar radius may reduce the amount that the proximal end 108 protrudes from the nose of the individual wearing the nasopharyngeal airway device 100 and may decrease the likelihood that the individual inadvertently removes the nasopharyngeal airway device 100 while sleeping or otherwise. However, the contour/curvature of the arced arm 130 and the contour/curvature of the proximal end 108 may alternatively be different. The projection 128 and the elongate body 102 form a clip 138. The clip 138 may be positioned about the septum of the individual after the elongate body 102 is inserted into the nose to secure the nasopharyngeal airway device 100. The clip 138 may alternatively be positioned about the ala of the nose.

Figure 2B:
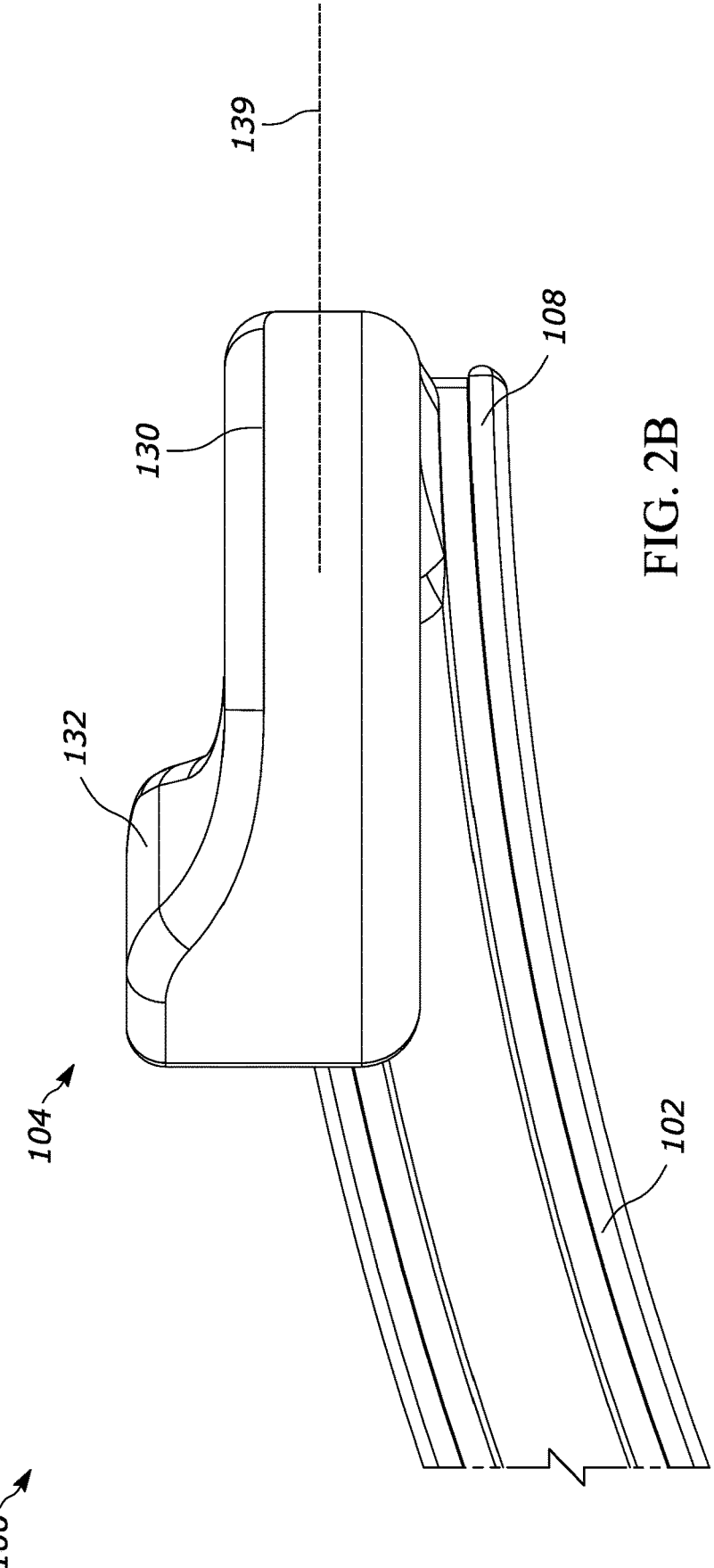
FIG. 2B is an enlarged isometric-side view of the proximal end of the nasopharyngeal airway device of FIG. 2A.

FIG. 2B is an enlarged isometric-side view of the proximal end 108 of the nasopharyngeal airway device 100 of FIG. 2A. FIG. 2B illustrates that the arced arm 130 substantially follows a reference plane 139. The reference plane 139 may be defined at the proximal end 108 of the elongate body 102. The elongate body 102 curves/arcs away from the reference plane 139 as the elongate body 102 moves toward the distal end 106 of the elongate body 102. In the example shown, a width of the foot 132 is greater than a width of the arced arm 130. Specifically, a top portion of the foot 132 as shown in FIG. 2B extends away from a top portion of the arced arm 130 while the lower portion of the foot 132 and the arced arm 130 are substantially flush with one another.

Figure 3A:
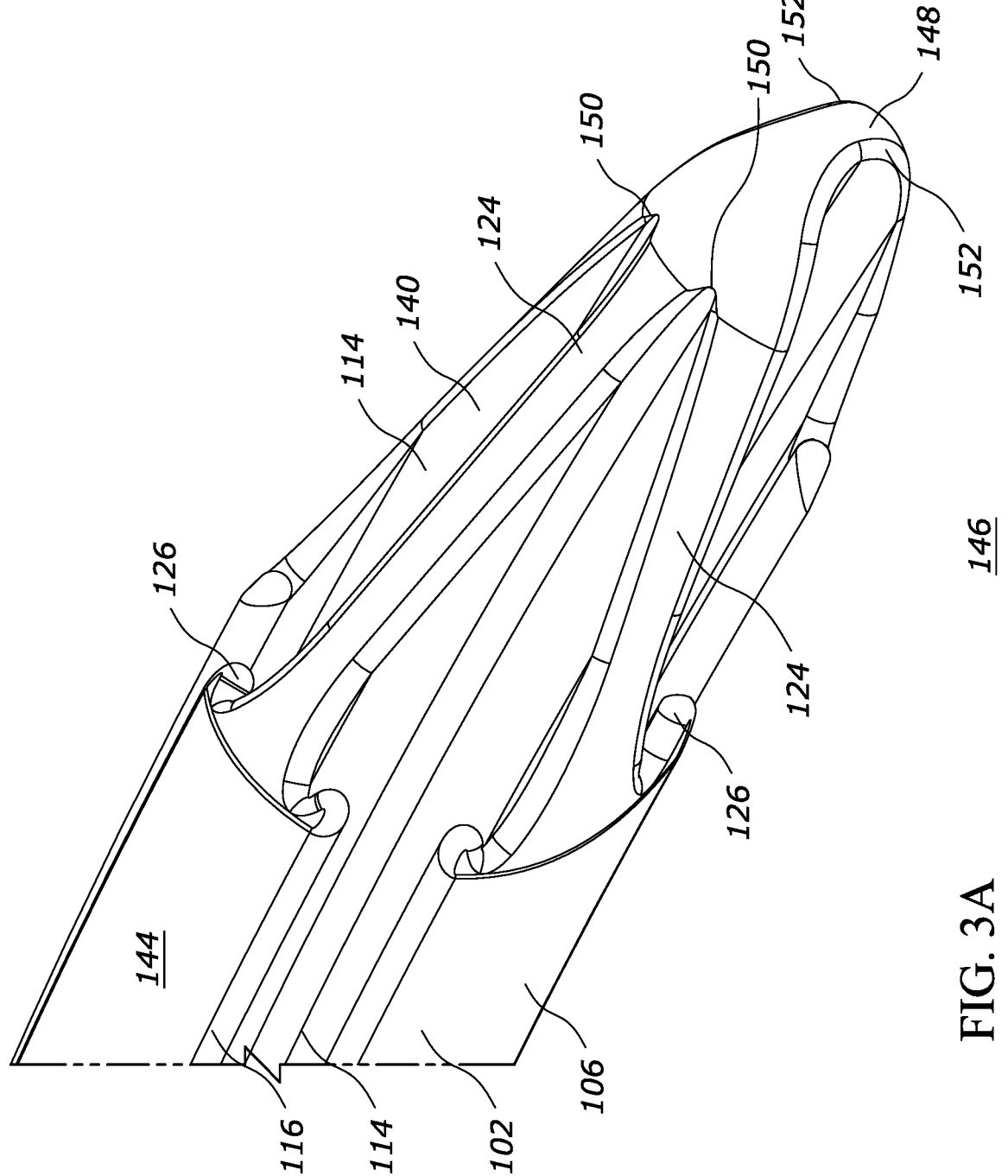
FIG. 3A is an enlarged isometric view of an alternative distal end of the nasopharyngeal airway device of FIG. 1A.
Figure 3B:
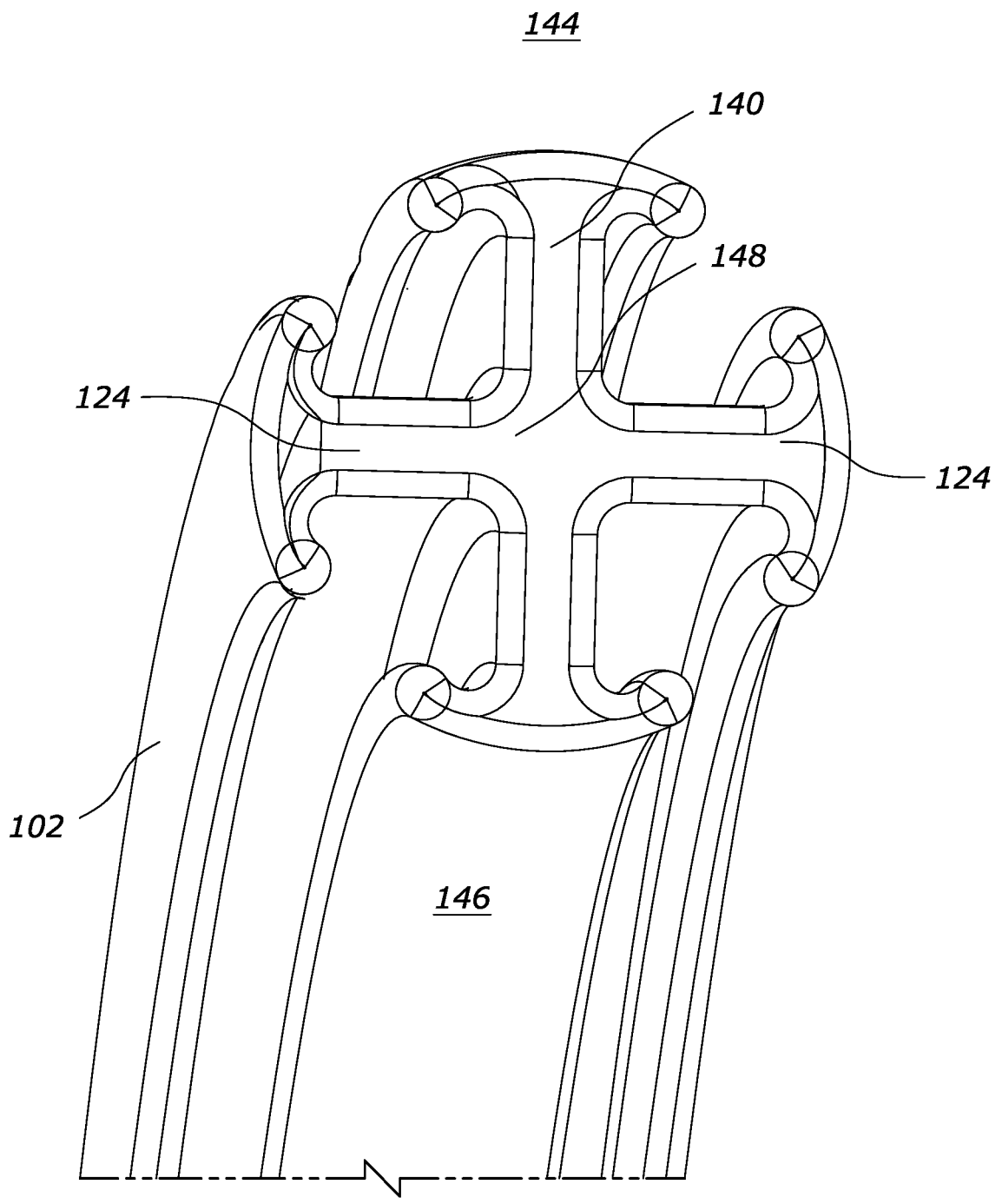
FIG. 3B is an enlarged isometric end view of the alternative distal end 106 of FIG. 3A.

FIG. 3A is an enlarged isometric view of an alternative distal end 106 of the nasopharyngeal airway device 100 of FIG. 1A. FIG. 3B is an enlarged isometric end view of the alternative distal end 106 of FIG. 3A. The distal end 106 of FIGS. 3A and 3B includes a tapered portion 140. The tapered portion 140 is similar to the rounded portion 122 of FIG. 1A but for the triangular portions 124 of the tapered portion 140 are off set from one another. For example, the triangular portion 124 adjacent a top portion 144 of the elongate body 102 may be offset relative to the triangular portion 124 adjacent a bottom portion 146 of the elongate body 102 to allow a tip 148 of the elongate body 102 to be formed. The tip 148 of the elongate body 102 is bulbous/rounded. In another example, an angle of the triangular portion 124 on the top portion 144 of the elongate body 102 may have a shallower approach toward the tip 148 of the elongate body 102 as compared to an angle of approach of the triangular portion 124 on the bottom portion 146 of the elongate body 102. In the example shown, upper-channel end portions 150 on the top portion 144 of the elongate body 102 terminate before lower-channel end portions 152 on the bottom portion 146 of the elongate body 102. The end portions 150, 152 may be differently arranged.

FIG. 4A is an isometric view of another nasopharyngeal airway device 200 in accordance with a second example of the present disclosure. FIG. 4B is an enlarged isometric view of the proximal end 108 of the nasopharyngeal airway device 200 of FIG. 4A. The nasopharyngeal airway device 200 of FIGS. 4A and 4B is similar to the nasopharyngeal airway device 100 of FIG. 1A. However, in contrast, the nasopharyngeal airway device 200 of FIGS. 4A and 4B includes a pair of the elongate bodies 102 and a bridge 202 that couples the elongate bodies 102 together. In the example shown, the bridge 202 is coupled to inward facing flanges 118 of the elongate bodies 102. The bridge 202 may be adapted to hold the nasopharyngeal airway device 200 in place and prevent/deter the nasopharyngeal airway device 200 from moving to an undesired position. The elongate bodies 102 are the same or similar lengths in the example shown. Alternatively, the elongate bodies 102 may be different lengths (see, for example, FIG. 5).

FIG. 5 is an isometric view of another nasopharyngeal airway device 300 in accordance with a third example of the present disclosure. The nasopharyngeal airway device 300 of FIG. 5 is similar to the nasopharyngeal airway device 200 of FIG. 4A. However, in contrast, the nasopharyngeal airway device 300 of FIG. 5 includes elongate bodies 102 that have different lengths. The longer one of the elongate bodies 102 may be adapted to be fully inserted into the nasal cavity. The shorter one of the elongate bodies 102 may be adapted to be secured within the other one of the nostrils but may not extend into a nasal cavity as far as the longer one of elongate bodies 102. In example shown, each of the elongate bodies 102 has a cross-section at the proximal end 108 that is substantially the same. In another example, the elongate bodies 102 may include a different cross-section from one another. In such an example, the proximal ends 108 and the associated securement component 104 may be adapted to secure the nasopharyngeal airway device 300 relative to the nostrils of an individual.

FIG. 6A is an isometric view of another nasopharyngeal airway device 400 in accordance with a fourth example of the present disclosure. FIG. 6B is an enlarged isometric view of the proximal end 108 of the nasopharyngeal airway device 400 of FIG. 6A. FIG. 6C is an enlarged isometric view of the distal end 106 of the nasopharyngeal airway device 400 of FIG. 6A.

The nasopharyngeal airway device 400 of FIGS. 6A, 6B, and 6C is similar to the nasopharyngeal airway device 100 of FIG. 1A. However, in contrast, the nasopharyngeal airway device 400 of FIGS. 6A, 6B, and 6C includes a tubular portion 402. The tubular portion 402 is disposed on the proximal end 108 of the elongate body 102. The elongate body 102 also includes a transition portion 403 where the ribs 112 transition to the tubular portion 402. The tubular portion 402 and/or the transition portion 403 may in be a different position.

Referring to FIG. 6B, the proximal end 108 of the nasopharyngeal airway device 400 includes a tubular wall 404 that surrounds the hub 110 and the ribs 112. The nasopharyngeal airway device 400 includes three ribs 112 instead of the four ribs 112 disclosed in the examples above. The ribs 112 may extend through a majority of the nasopharyngeal airway device 400. However, in other examples, the hub 110 and the ribs 112 may not be provided in at least a portion of the elongate body 102 (see, for example, FIG. 7B).

FIG. 7A is an isometric view of another nasopharyngeal airway device 500 in accordance with a fifth example of the present disclosure. FIG. 7B is an enlarged isometric view of the proximal end 108 of the nasopharyngeal airway device 500 of FIG. 7A. FIG. 7C is an enlarged isometric view of the distal end 106 of the nasopharyngeal airway device 500 of FIG. 7A.

The nasopharyngeal airway device 500 of FIGS. 7A, 7B, and 7C is similar to the nasopharyngeal airway device 400 of FIG. 6A. However, in contrast, the nasopharyngeal airway device 500 of FIGS. 7A, 7B, and 7C includes a closed rounded end 502. The end 502 is solid and may be adapted to facilitate easier insertion of the elongate body 102 into a nostril. A wall 504 of the end 502 defines a portion of the channel 114 and may be adapted to further distribute airflow. Moreover, the wall 504 may be a stop that is engagable by a suction device, an endoscope, or any other device inserted into the channel 114 of the nasopharyngeal airway device 500 from the proximal end 108 and moved toward the distal end 106, for example.

Referring to FIG. 7B, the proximal end 108 of the nasopharyngeal airway device 500 includes the tubular wall 404. However, in the example shown, the hub 110 and the ribs 112 are not provided in at least a portion of the tubular portion 402.

FIG. 8 is an isometric view of another nasopharyngeal airway device 600 in accordance with a sixth example of the present disclosure. The nasopharyngeal airway device 600 includes three ribs 112 that form the channels 114 having the lateral opening 117. In contrast to the examples disclosed above, in the implementation shown, the channels 114 include a straight-channel portion 602 adjacent the proximal end 108 and a non-linear, e.g., helical-channel portion 604 adjacent the distal end 106. The helical-channel portion 604 is formed at least partially by the distal flanges 118 that twist down at least a portion of the nasopharyngeal airway device 600. Providing the nasopharyngeal airway device 600 with the helical-channel portion 604 reduces the likelihood and an amount that one of the lateral openings 117 becomes blocked by, for example, the anatomy of the individual when wearing the device 600 such as by the tongue. While the straight-channel portion 602 is shown being approximately one third of the entire length of the nasopharyngeal airway device 600 and the helical-channel portion 604 is shown being approximately two thirds of the entire length of the nasopharyngeal airway device 600, the length of the straight-channel portion 602 may be more of the entire length, less of the entire length, or omitted.

FIG. 9A is an isometric view of another nasopharyngeal airway device 700 in accordance with a seventh example of the present disclosure. In contrast to the examples disclosed above, the nasopharyngeal airway device 700 includes the elongate body 102 having an outer surface 702 that forms a single open channel 114 that extends between the distal end 106 and the proximal end 108. The lateral opening 117 of the channel 114 can be closed when a compressive force is applied to sides 704 of the elongate body 102 in a direction generally indicated by arrows 706 creating a tubular portion. Thus, a portion of the lateral opening 117 may be closed and form a tubular flow path in, for example, a higher-compression area where stenting is included and another portion of the lateral opening 117 may be open in a lower-compression area providing an open flow through the lateral opening 117. The lateral openings 117 reduce an amount of force required to move air through the nasopharyngeal airway device 700 for breathing and/or disperse the air flow more evenly within the airway of the individual wearing the nasopharyngeal airway device 700.

FIG. 9B is an isometric end-view of the distal end 106 of the nasopharyngeal airway device 700 of FIG. 9A. In the implementation shown, the sides 704 of nasopharyngeal airway device 700 include edges 707 that form the lateral opening 117 and include inward facing stops 708. The stops 708 are formed by a thicker portion 710 of the elongate body 102 and have flat surfaces 711 that are positioned to abut one another when the lateral opening 117 is closed. Having the stops 708 abut one another deters the edges 707 from sliding past one another when the elongate body 102 is under radial compression and maintains a threshold diameter 712 of the channel 114. While the stops 708 are shown including the flat surfaces 711, in other implementations, the stops 708, may include corresponding contours such as including complementary male and female portions.

FIG. 10 is an isometric view of another implementation of the nasopharyngeal airway device 700 of FIGS. 9A and 9B. The nasopharyngeal airway device 700 of FIG. 10 is similar to the nasopharyngeal airway device 700 of FIGS. 9A and 9B. However, in contrast, the distal end 106 of the nasopharyngeal airway device 700 of FIG. 10 includes a fillet 713 that eases insertion of the nasopharyngeal airway device 700 into the nasal airway of an individual. Moreover, the elongate body 102 of FIG. 10 has a reduced radius of curvature along its length as compared to some of the other examples disclosed to position the elongate body 102 of FIG. 10 adjacent the back of the throat and away from the tongue and uvula of the individual. Advantageously, positioning the elongate body 102 toward the back of the throat allows the individual to more easily swallow while wearing the nasopharyngeal airway device 700, and helps avoid potential air concentration at the back of the throat.

The radius of curvature of the nasopharyngeal airway device 700 of FIG. 10 or any of the disclosed examples may be between a straight device and approximately 40 millimeters (mm), between approximately 150 mm and approximately 60 mm, between approximately 60 mm and 500 mm, and/or approximately 140 mm. While not shown, the nasopharyngeal airway device 700 of FIG. 10 or any of the disclosed examples may include one or more transverse holes through the elongate body 102 or otherwise fenestrated to increase air flow (e.g., similar to a Murphy's eye).

FIG. 11 is an isometric view of another implementation of the nasopharyngeal airway device 700 of FIGS. 9A and 9B. The nasopharyngeal airway device 700 of FIG. 11 is similar to the nasopharyngeal airway device 700 of FIGS. 9A and 9B. However, in contrast, the nasopharyngeal airway device 700 of FIG. 11 has an interior surface 714 forming a spiral protrusion 716 that increases the strength of the elongate tube 102 and deters the elongate tube 102 from inwardly collapsing while still allowing the elongate tube 102 to have sufficient flexibility to ease insertion into the nasal airway of an individual. However, in other implementations, the interior surface 714 is smooth such as the interior surface of the nasopharyngeal airway device 700 of FIGS. 9A and 9B.

FIG. 12 is an isometric view of another implementation of the nasopharyngeal airway device 700 of FIGS. 9A and 9B. The nasopharyngeal airway device 700 of FIG. 12 is similar to the nasopharyngeal airway device 700 of FIGS. 9A and 9B. However, in contrast, the nasopharyngeal airway device 700 of FIG. 12 includes the tubular portion 402 disposed on the distal end 106. The tubular portion 402 increases the strength of the elongate body 102 and the lateral opening 117 increases airflow through the nasopharyngeal airway device 700. While the tubular portion 402 is approximately one quarter of the entire length of the nasopharyngeal airway device 700 and the lateral opening 117 extends approximately three quarters of the entire length of the nasopharyngeal airway device 700, the length of the tubular portion 402 may be more of the entire length, less of the entire length, or omitted as shown in FIGS. 9A and 9B. While the tubular portion 402 is shown extending from the distal end 106, in other implementations, the tubular portion 402 may extend from the proximal end 108 or may be disposed in any location, such as being centrally located or otherwise off set from the ends 106, 108, along the elongate body 102.

FIG. 13 is an isometric view of another implementation of the nasopharyngeal airway device 700 of FIGS. 9A and 9B. The nasopharyngeal airway device 700 of FIG. 13 is similar to the nasopharyngeal airway device 700 of FIGS. 9A and 9B. However, in contrast, the edges 707 of the elongate body 102 that form the lateral opening 117 include opposing cutouts 718 that are spaced from one another by the inward facing stops 708. The cutouts 718 allow airflow therethrough even when the adjacent inward facing stops 708 engage one another in response to a compressive force being applied to the sides 704 in the direction generally indicated by arrows 706. The cutouts 718 are shown as being substantially uniform and consistently spaced. However, the cutouts 718 may be differently formed and/or spaced. For example, the cutouts 718 may be larger and/or have a trapezoidal shape as shown in FIG. 14. Moreover, the cutouts 718 may be defined along less of the lateral opening 117 or omitted and may be provided on any of the implementations disclosed herein including, for example, the nasopharyngeal airway device 100 of FIG. 1A.

FIG. 14 is an isometric view of another implementation of the nasopharyngeal airway device 700 of FIGS. 9A and 9B. The nasopharyngeal airway device 700 of FIG. 14 is similar to the nasopharyngeal airway device 700 of FIG. 13. However, in contrast, the distal end 106 of nasopharyngeal airway device 700 of FIG. 14 includes the fillet 713 that eases insertion of the nasopharyngeal airway device 700 into the nasal airway of an individual. The cutouts 718 of the nasopharyngeal airway device 700 have a trapezoidal shape. However, the cutouts 718 may have any other suitable shape including providing different shapes and/or sizes of the cutouts 718 along the lateral opening 117.

FIG. 15 is an isometric view of another implementation of the nasopharyngeal airway device 700 of FIGS. 9A and 9B. The nasopharyngeal airway device 700 of FIG. 15 is similar to the nasopharyngeal airway device 700 of FIG. 14. However, in contrast, the distal end 106 of nasopharyngeal airway device 700 of FIG. 15 includes a hood or partially closed rounded end 720 that eases insertion of the nasopharyngeal airway device 700 into the nasal airway of an individual. In some implementations, an inner surface 722 at the distal end 106 of the elongate body 102 defines a portion the channel 114 and forms a stop 724 that can be engaged by a suction device or an endoscope, advantageously preventing the suction device or scope from extending into the airway beyond the stop 724. The device is insertable through the proximal end 108 and into the channel 114 of the nasopharyngeal airway device 700. Providing the stop 724 may allow an individual to self-suction the nasopharyngeal airway device 700 and wear the nasopharyngeal airway device 700 for longer periods of time. The inner surface 722 and the associated stop 724 may be tapered to facilitate fluid flow out of the channel 117 or may be rounded or may be a right angle.

FIG. 16 is an isometric detailed view of another implementation of the nasopharyngeal airway device 700 of FIGS. 9A and 9B. The nasopharyngeal airway device 700 of FIG. 16 is similar to the nasopharyngeal airway device 700 of FIG. 15. However, in contrast, the distal end 106 of nasopharyngeal airway device 700 of FIG. 16 has a partially closed rounded end 720 that is slightly more closed or bulbous than the rounded end 720 of the nasopharyngeal airway device 700 of FIG. 15. While the partially closed rounded end 720 is shown having a particular configuration, the end 720 may be closed further or less or otherwise formed to direct air flowing into and out of the channel 117 of the elongate body 102. Moreover, the leading lower edges 725 of the elongate body 102 may extend further forward or rearward toward the proximal end 108 or may otherwise have a contour to provide surface tension reducing protrusions.

FIG. 17A is an isometric view of another implementation of the nasopharyngeal airway device 700 of FIGS. 9A and 9B. The nasopharyngeal airway device 700 of FIG. 17A is similar to the nasopharyngeal airway device 700 of FIG. 15. However, in contrast, the distal end 106 of nasopharyngeal airway device 700 of FIG. 17 includes a fully closed rounded end 726 as opposed to the partially closed rounded end 720 of FIG. 15. The fully closed rounded end 726 prevents air from flowing out of the distal end 106 itself and ensures that air flows instead flows into and out of the lateral openings 117, thereby dispersing the air flow in a manner that deters the individual using the nasopharyngeal airway device 700 from obtaining a sore throat.

FIG. 17B is an isometric detailed view of the nasopharyngeal airway device 700 of FIG. 17A showing the fully closed rounded end 726. The nasopharyngeal airway device 700 of FIG. 17B also shows the stop 724, the cutouts 718, and the opposing stops 708 that engage each other when the elongate body 102 is radially compressed.

FIG. 18 is an isometric view of another implementation of the nasopharyngeal airway device 700 of FIGS. 9A and 9B. The nasopharyngeal airway device 700 of FIG. 17A is similar to the nasopharyngeal airway device 700 of FIGS. 17A and 17B. However, in contrast, the securement component 104 of the nasopharyngeal airway device 700 of FIG. 18 includes a pair of projections 128, with the first projection 128 including the arced arm 130 and the distal foot 132 positionable in the right nostril (specifically, within the superior nasal vestibule) and the second projection 128 extending from the elongate body 102 and positionable to be within, for example, the left nostril. When the securement component 104 is positioned within the nostrils of the individual, the projections 128 may form a form-fit nasal prong that allows the individual to breath out of nostrils.

While several examples have been disclosed herein, any features from any examples may be combined with or replaced by other features from other examples. Moreover, while several examples have been disclosed herein, changes may be made to the disclosed examples without departing from the scope of the claims.

What is claimed is:

1. A nasopharyngeal airway device, comprising:
an elongate body having a distal end and a proximal end, the elongate body having an outer surface defining one or more open channels extending along the elongate body between the distal end and the proximal end, each channel has a lateral opening that at least one of a) extends continuously longitudinally from the distal end to the proximal end, b) extends continuously longitudinally along at least half of the elongate body, or c) extends continuously along the elongate body from the proximal end to a location beyond a midpoint of the elongate body; and
a securement component securely coupled to the elongate body, wherein the securement component includes a rounded projection, the projection having a circular or oblong cross-section at a plane parallel to the outer surface of the elongate body, the projection extending perpendicularly from the outer surface of the elongate body, the projection spaced from the proximal end of the elongate body, the securement component being configured to secure the nasopharyngeal airway device within a nostril of an individual, the projection adapted to be inserted into the nostril.

2. The nasopharyngeal airway device of claim 1, wherein the one or more channels comprise at least one of a straight-channel portion or a helical pattern portion.

3. The nasopharyngeal airway device of claim 1, wherein the one or more channels comprises a single channel.

4. The nasopharyngeal airway device of claim 3, wherein the elongate body includes edges having opposing inward facing stops that define a lateral opening.

5. The nasopharyngeal airway device of claim 4, wherein the stops have at least one of flat surfaces or corresponding contours that are positioned to abut one another.

6. The nasopharyngeal airway device of claim 3, wherein the elongate body has a smooth inner surface that defines the channel or has an inner surface that defines the channel and has a spiral protrusion.

7. The nasopharyngeal airway device of claim 3, wherein the elongate body has a lateral opening that extends longitudinally along at least half of the elongate body.

8. The nasopharyngeal airway device of claim 7, wherein the elongate body includes edges that form the lateral opening and have cutouts and inward facing stops that are positioned to abut one another.

9. The nasopharyngeal airway device of claim 8, wherein the cutouts have a trapezoidal shape.

10. The nasopharyngeal airway device of claim 8, wherein the distal end has a partially-closed rounded end.

11. The nasopharyngeal airway device of claim 10, wherein an inner surface of the elongate body defining the channel forms a stop adapted to be engaged by a suction device or an endoscope.

12. The nasopharyngeal airway device of claim 1, further comprising lubricant within packaging in which the nasopharyngeal airway device is disposed or on the elongate body.

* * * * *